(12) United States Patent
Curry et al.

(10) Patent No.: US 7,850,981 B2
(45) Date of Patent: Dec. 14, 2010

(54) IMMUNO-ADJUVANT PDT TREATMENT OF METASTATIC TUMORS

(75) Inventors: Patrick Mark Curry, Vancouver (CA); Anna M. Richter, Vancouver (CA); Julia G. Levy, Vancouver (CA); David W. C. Hunt, White Rock (CA)

(73) Assignees: QLT, Inc., Vancouver, BC (CA); University of British Columbia (UBC), Vancouver (CA)

(*) Notice: Subject to any disclaimer, the term of this patent is extended or adjusted under 35 U.S.C. 154(b) by 328 days.

(21) Appl. No.: 10/985,582

(22) Filed: Nov. 9, 2004

(65) Prior Publication Data

US 2005/0187207 A1    Aug. 25, 2005

Related U.S. Application Data

(63) Continuation of application No. 09/756,687, filed on Jan. 9, 2001, now abandoned, which is a continuation-in-part of application No. 09/556,833, filed on Apr. 21, 2000, now abandoned.

(60) Provisional application No. 60/139,519, filed on Apr. 23, 1999.

(51) Int. Cl.
*A61K 45/00* (2006.01)

(52) U.S. Cl. ............ 424/278.1; 424/282.1; 514/410; 514/185; 607/88

(58) Field of Classification Search .............. 424/278.1, 424/282.1; 514/410, 185; 607/88
See application file for complete search history.

(56) References Cited

U.S. PATENT DOCUMENTS

| 4,436,727 A | 3/1984 | Ribi |
| 4,866,034 A | 9/1989 | Ribi |
| 4,883,790 A | 11/1989 | Levy et al. |
| 4,912,094 A | 3/1990 | Myers et al. |
| 4,920,143 A | 4/1990 | Levy et al. |
| 5,095,030 A | 3/1992 | Levy et al. |
| 5,149,527 A | 9/1992 | Weisenthal |
| 5,171,741 A | 12/1992 | Dougherty |
| 5,171,749 A | 12/1992 | Levy et al. |
| 5,308,608 A | 5/1994 | Dolphin et al. |
| 5,405,957 A | 4/1995 | Tang et al. |
| 5,512,675 A | 4/1996 | Tang et al. |
| 5,703,230 A | 12/1997 | Boyle et al. |
| 5,726,304 A | 3/1998 | Tang et al. |
| 5,747,475 A | 5/1998 | Nordquist et al. |
| 5,756,541 A | 5/1998 | Strong et al. |
| 5,759,554 A | 6/1998 | Alkemade et al. |
| 5,770,619 A | 6/1998 | Richter et al. |
| 5,831,088 A | 11/1998 | Dolphin et al. |
| 5,880,145 A | 3/1999 | Sternberg et al. |
| 5,883,246 A | 3/1999 | Bruckner et al. |
| 5,929,105 A | 7/1999 | Stemberg et al. |
| 5,990,149 A | 11/1999 | Stemberg et al. |
| 6,071,944 A | 6/2000 | Rodgers et al. |
| 6,149,671 A | 11/2000 | Nordquist et al. |
| 6,290,712 B1 | 9/2001 | Nordquist et al. |

FOREIGN PATENT DOCUMENTS

| WO | WO-96/31237 | 10/1996 |
| WO | WO-99/47162 | 9/1999 |

OTHER PUBLICATIONS

Fisher et al. (Lasers Surg. Med. 1995; 17 (1): 2-31).*
Jori et al., J. Photochem. Photobiol. B: Biol. (1990) 6:93-101.
Brasel et al., Blood (1996) 88:2004-2012.
Burger et al., Annals of Surgical Oncology (1996) 3:580-587.
Chakravarty et al., Cancer Res. (1999) 59(24):6028-6032.
Chen et al., Cancer Letters (1997) 115:25-30.
Chen et al., Cancer Res. (1997) 57(16):3511-3516.
Chen et al., Proc SPIE-Int SOCOPT Eng (1998) 3254:27-34.
Chen et al., Cancer J. (2002) 8:154-163.
Cho et al., J Urol (1992) 147:743-6.
Ciavarra et al., Cancer Res. (2000) 60:2081-2084.
Cox et al., Vaccine (1987) 15:248-56.
Dougherty et al., Journal of the National Cancer Institute (1975) 55:115-119.
Esche et al., Cancer Res (1998) 58:380-383.
Evans et al., Journal of the National Cancer Institute (1990) 82:34-39.
Fingar et al., Cancer Research (1990) 50:2599-2603.
Fischer et al., J. Photochem Photobiol B (1998) 43(1):27-33.
Gore and Riches, (1996) The History of Immunotherapy, in Gore and Riches, (eds.), Immunotherapy in Cancer, John Wiley & Sons, Chichester, pp. 1-9.
Granville et at., Photochem Photobiol (1998) 67:358-62.
Hartwell et al., Science (1997) 278:1064-1068.
Jacobsen et al., J Exp Med (1995) 181:1357-1363.
Jain, Sci Am (1994) 271(1):58-65.
Johnston et al., J Nat'l Cancer Inst. (1991) 83(17):1240-1245.
Karrer et al., Dtsch Med Wochenschr (1997) 122(37):1111-1114 (English Abstract).
Korbelick et al., Proceedings of the International Conference on Photodynamic Therapy and Medical Laser Applications, XX,XX Jun. 24, 1992, pp. 518-520.
Korbelik et al., Proc. SPIE (1993) 1616:192-198.
Korbelik, J Clin Laser Med Surg (1996) 14:329-334.
Korbelik et al., British Journal of Cancer (1997) 75:202-207.
Korbelik et al., Photochem Photobiol. (1994) 60(5):497-502.
Korbelik et al., Photochem Photobiol (2001) 73(4):403-409.
Korbelik et al., Cancer Lett (1999) 137:91-98.
Korbelik et al., Cancer Res (1996) 56(24):5647-5652.
Korbelik and Cecic, J Photochem Photobiol B (1998) 44:151-8.
Kresl et al., Tumour Biol. (1999) 20(2):72-87.
Krosl et al., Br J Cancer (1995) 71:549-555.
Krosl et al., Cancer Res. (1996) 56(14):3281-3286.
Krosl and Korbelik, Cancer Letters (1994) 84:43-49.
Lapes et al., J. Photochem Photobiol B (1996) 36(2):205-207.

(Continued)

*Primary Examiner*—Stephen L. Rawlings
(74) *Attorney, Agent, or Firm*—Morrison & Foerster LLP

(57) ABSTRACT

Immuno-adjuvant photodynamic therapy to treat and prevent metastatic cancer is effected using photosensitizers in combination with immuno-adjuvants to destroy metastatic tumor cells.

18 Claims, 4 Drawing Sheets

OTHER PUBLICATIONS

Lynch et al., Crit Rev Immunol. (1998) 18(1-2):99-107.
Lynch et al., Nat Med. (1997) 3(6):625-631.
Maraskovsky et al., J Exp Med (1996) 184:1953-1962.
Momma et al., Cancer Res. (1998) 58(23):5423-5431.
Myers et al., Urology (1989) 33:230-235.
Nsevo et al., Proceedings of the Society of Photo-Optical Instrumentation Engineers (1989) 1065:66-72.
Section 3: Treatment of Metastatic Cancer to Bone, in DeVita Jr. et al., (eds.), Cancer: Principles and Practice, J.B. Lippincott Company, Philadelphia, vol. 2, pp. 2298-2317, 2008.
Stetler-Stevenson et al., "Molecular Biology of Cancer: Invasion and Metastasis" in 1 Cancer: Principles and Practice of Oncology 123 (DeVita et al., eds. 6th Ed. 2001).
Van Hillegersberg et al., Br. J. Cancer (1995) 71(4):733-737.

* cited by examiner

IMMUNO-ADJUVANT PDT TREATMENT OF METASTATIC TUMORS

RELATED APPLICATIONS

This application is a continuation application of U.S. patent application Ser. No. 09/756,687, filed Jan. 9, 2001 (now abandoned), which is a continuation-in-part application of U.S. patent application Ser. No. 09/556,833, filed Apr. 21, 2000 (now abandoned), which claims benefit of priority from U.S. Provisional Application 60/130,519, filed Apr. 23, 1999, each of which are hereby incorporated by reference as if fully set forth.

FIELD OF THE INVENTION

The invention relates to the use of photodynamic therapy (PDT) treatment in combination with immuno-adjuvants to treat metastatic tumors. This provides a novel treatment modality termed photodynamic vaccination, or PDV. The PDV may be conducted with any photosensitizer, but combinations comprising a benzoporphyrin derivative (BPD) are preferred for such PDV treatment.

DESCRIPTION OF THE RELATED ART

This invention relates to metastatic cancer. The metastatic process, which results in the growth of secondary tumors at sites distal to the primary tumor, is the cause of death in most cancers (Poste and Fidler, 1980). Although most patients with newly diagnosed solid tumors are free of detectable metastases, and about half of those patients can be cured of their disease by local cancer treatment, the remaining patients have clinically occult micrometastases that will become evident with time. Thus, at the time of primary tumor treatment, the total percentage of patients with either detectable metastases or microscopic disseminated disease is 60% (Liotta and Stetler-Stevenson, 1989).

The brain is the most favored site for metastatic spread, occurring in 25% to 30% of all cancer patients: the most frequent primary cancers, lung cancer, breast cancer and melanoma, are associated with high incidence of brain metastases (Wright and Delaney, 1989). The lung is the second most common site of metastatic spread and pulmonary metastases most frequently originate from bone and soft-tissue sarcomas (Roth, 1989). Liver metastases commonly result from gastrointestinal tract tumors (Sugarbaker and Kemeny, 1989) and bone metastases from breast, lung and kidney primary tumors (Malawer and Delaney, 1989).

Management of a significant number of cancer cases, therefore, depends upon treating multiple tumors, traditionally through the use of surgery, radiation therapy, chemotherapy, or adjuvant therapies consisting of combinations of the three modalities.

Observations relating to tumor immunity have provided a focal point for the development of possible tumor therapy. Prehn and Main showed in 1957 that chemically induced tumors of mice were antigenic. There has been controversy concerning the relevance of chemically induced tumors, which are generally immunogenic, compared with spontaneously arising tumors in mice and human tumors which are not (Hewitt, 1979; Hewitt et al., 1976).

The issue was addressed by Boon et al. who showed that mutagenized antigenic variants of non-immunogenic tumors could generate immunological protection in mice against the parent tumor; that is, the mutagenized and parent tumors shared antigens (Boon et al., 1994). The results suggested that spontaneous experimental tumors and human tumors were antigenic and could be made immunogenic through the appropriate augmentation of the immune system (Boon et al., 1994). Subsequent studies confirmed that the immune system could be made to recognize weakly immunogenic tumors by transforming tumor cells with genes for the expression of cytokines, co-stimulatory molecules, or MHC molecules (Gajewski et al., 1995; Pardoll, 1993).

Also, in vitro culture of tumor-infiltrating lymphocytes from tumor-bearing mice and cancer patients with cytokines and irradiated tumor cells, and re-infusion of the activated lymphocytes can result in tumor regression (Burger et al., 1996; Schultze et al., 1997). Finally, tumor antigens recognized by the cells of the immune system have been identified in both animal models and human tumors (Jaffee and Pardoll, 1996). Tumor antigens recognized by T lymphocytes in human melanomas are the most fully characterized set of tumor antigens and may be non-mutated, widely distributed molecules, unique and mutated proteins, or normal proteins that are overexpressed in tumors (Robbins and Kawakami, 1996).

One result from the observations concerning tumor immunity is cancer immunotherapy. For centuries it has been observed that many types of diseases, including cancer, can be improved or even cured following attacks of erysipelas, an acute skin infection. In 1909 William Coley reported several positive results following deliberate infection of cancer patients with bacteria in order to induce erysipelas. Although the contemporary theory explained tumor improvements or cures as the result of toxic products released during the bacterial infection, Coley's approach to cancer treatment may be regarded as the first instance of "biotherapy" (the original term) or cancer immunotherapy.

Immunotherapy of cancer, in which the immune system is modulated through the use of specific and non-specific tumor vaccines, bioactive molecules such as cytokines, or adoptive transfer of activated lymphocytes is one of the most appealing approaches to the treatment of metastatic cancers. The therapy is based on the concept that the patient's immunological tolerance of their cancer can be broken so that the cancer is recognized as foreign by the patient's immune system (Gore and Riches, 1996).

Another tumor treatment method is photodynamic therapy (PDT). PDT is based upon dye-sensitized photooxidation of diseased tissue and was originally developed as a treatment modality for solid tumors (Dougherty et al., 1975). Singlet oxygen ($^1O_2$) is generated, without radical formation, through energy transfer processes from light-activated photosensitizer molecules in the "type II mechanism", and it is widely accepted that $^1O_2$ is responsible for the primary photodynamic effect in vivo (Weishaupt et al., 1976). Membrane damage brought about by $^1O_2$-mediated lipid peroxidation leading to loss of cell integrity is thought to be the primary mode of cell killing by PDT (Henderson and Dougherty, 1992), although metabolically regulated processes may also be involved in PDT-induced damage and cell death (Granville et al., 1998; Tao et al., 1996).

Photosensitizers are usually delivered intravenously and selective destruction of tumor tissue is based upon preferential uptake of the drug by neoplastic tissue and localized exposure of the tumor to the wavelength of light best suited to tissue penetration and photosensitizer activation. Necrosis of tumor tissue is a result of the direct effects of $^1O_2$ on tumor cells, and also from the anoxic conditions that develop in the tumor following disruption of tumor vasculature by PDT (Henderson et al., 1985).

Following PDT, immune responses are initiated with the rapid induction of an inflammatory reaction (Henderson and Dougherty, 1992; Ochsner, 1997) involving the release of cytokines (Evans et al., 1990; Gollnick et al., 1997; Nseyo et al., 1989), eicosanoids (Fingar et al., 1991; Henderson and Donovan, 1989), and clotting factors (Fingar et al., 1990; Foster et al., 1991), and progresses to the activation of immune cells (Qin et al., 1993; Yamamoto et al., 1992; Yamamoto et al., 1994) and infiltration of immune cells into PDT-treated tissue (Korbelik et al., 1996). For example, tumor cells pre-treated with PDT in vitro were sensitized to macrophage-mediated lysis (Korbelik et al. 1994) and at low photosensitizer levels, PDT activated macrophage phagocytic activity (Yamamoto et al. 1994). PHOTOFRIN®-based PDT stimulated the release of the immunomodulatory molecules prostaglandin-E2 (Henderson et al. 1989) and tumour necrosis factor-α (TNF-α) (Evans et al. 1990) from murine macrophages. PHOTOFRIN® and light treatment induced the expression of interleukin (IL) IL-6 in HeLa cells (Kick et al. 1995) and within mouse tumours (Gollnick et al. 1997). A massive and rapid influx of granulocytes and macrophages has been described for murine tumours treated with PHOTOFRIN® and light [Golnick et al. 1997; Korbelik 1996; Krosl et al. 1995)]. PDT has been described as inducing tumor immunity (Korbelik 1996) which may be augmented by the localized administration of an adjuvant at the time of photo-irradiation (Korbelik et al. 1998). Moreover, granulocyte-macrophage colony stimulating factor (GM-CSF) administered in three doses at two-day intervals, commencing 48 hours before light-irradiation, improved the curative effect of PHOTOFRIN® and verteporfin-mediated PDT against mouse tumours (Krosl et al. 1996).

PDT has also been shown to enhance both phagocytosis and tumor cytotoxicity when normal mouse peritoneal macrophages were treated in vitro (Yamamoto et al., 1992; Yamamoto et al., 1994) and similar treatments caused the secretion of tumor necrosis factor (TNF) (Evans et al., 1990). In the clinical setting, treating bladder cancer with PDT resulted in detectable levels of interleukin (IL-1) and TNF-α in the urine of patients within 3 hours of treatment and IL-2 within 24 h in a profile that resembled treatment of bladder cancer with Bacille Calmette Guérin (BCG). In BCG therapy, elevated cytokine levels were associated with improvement (Evans et al., 1990).

The role of the host immune system in PDT-mediated tumor eradication has recently been examined by Korbelik et al. by comparing the response to PDT of a solid tumor grown in immunocompetent or immunodeficient mice. PDT cured all normal mice; however, using the same treatment protocol with nude mice (which have a congenital absence of the thymus, resulting in reduced numbers of T cells but normal levels of B and NK cells) or scid mice (which are unable to complete V(D)J recombinations during T and B cell development and have no mature T and B cells), the initial tumor ablation following PDT was followed by regrowth of all of the tumors. Transferring splenic T cells to scid mice or reconstituting lethally irradiated scid mice with normal mouse bone marrow prior to PDT resulted in delayed regrowth or tumor cure (Korbelik et al., 1996).

The same group observed a 200-fold increase in the number of tumor-associated neutrophils within minutes of suboptimal photodynamic treatment and a drop in neutrophil content to near control levels at 2 hours after light treatment (Krosl et al., 1995). Infiltrating mast cell numbers also increased within 5 min of light treatment and the higher level of mast cells was maintained for 4 hours after PDT. The numbers of mast cells were, however, several logs lower than the numbers of neutrophils. Approximately 10% of the total number of cells in the tumor at 2 hours after PDT were characterized as monocytes that had invaded the tumor from the circulation.

Also, there was a large population (20% of total cells) of tumor-associated macrophages in untreated tumors. Resident macrophages were equally sensitive to PDT killing as malignant cells but following PDT, tumor associated macrophages were shown to be almost 5 times more cytotoxic against tumor target cells in vitro, compared with macrophages isolated from untreated tumors.

Another means of stimulating the host immune response is by the use of adjuvants. Any material that increases the immune response towards an antigen is referred to as an adjuvant (see Appendix A) and while they have been used for at least 70 years in the production of traditional vaccines designed to prevent infectious diseases, adjuvants are also being developed for use in cancer vaccines. Adjuvants are able to augment immune responses through several mechanisms including: 1) causing depot formation at the site of inoculation; 2) acting as delivery vehicles which may target antigens to cells of the immune system; 3) acting as immune system stimulators.

Many of the adjuvant preparations function via several of these mechanisms. The ideal adjuvant would have safe local and systemic reactions (which would preclude general toxicity, autoimmune and hypersensitivity reactions, and carcinogenicity) be chemically defined so consistent manufacture is possible, would enhance protective (or in the case of cancer vaccines, therapeutic) immunity towards weak antigens, and would be biodegradable (Audibert and Lise, 1993; Cox and Coulter, 1997; Gupta and Siber, 1995).

The prototypical adjuvant, which is also the most potent, is Freund's Complete Adjuvant (CFA) developed in 1937 by Jules Freund. CFA consists of a preparation of killed *Mycobacterium tuberculosis* dispersed in mineral oil. When emulsified with water soluble antigens, the vaccine stimulates both humoral (antibody-mediated) and cell-mediated immunity towards the antigens. The use of this adjuvant may result in serious side effects including organ injury via granuloma formation and autoimmune disease, and its use is restricted even in experimental animals. Incomplete Freund's Adjuvant (IFA), which lacks the mycobacterial component of CFA, is less toxic but does not enhance cell-mediated immunity. Nonetheless, IFA is currently undergoing clinical trials in cancer vaccine formulations (for example NCI-T97-0110, NCI-98-C-0142, NCI-H98-0010, NCI-T96-0033).

New adjuvants, such as the Ribi Adjuvant System (RAS) have been designed to substitute highly purified bacterial components for *M. tuberculosis* in order to maintain the immune stimulatory properties of CFA without the side effects. A variation of RAS, DETOX™ adjuvant, is currently in clinical trials as a component of cancer vaccines (NCI-V98-1489, NCI-96-C-0139). Others, such as Hunter's TITERMAX™, which is has not been approved for clinical use but has been extensively characterized in animal systems, use completely synthetic compounds.

There have been previous attempts to combine immuno-adjuvants and PDT. Myers et al. injected formalin killed bacteria, *Corynebacterium parvum*, intralesionally in experimental tumors 24 hours prior to PDT in the first reported case of immuno-adjuvant PDT. The therapy improved the efficacy of hematoporphyrin derivative (Hpd)-sensitized PDT as measured by reduction in tumor volume and prolongation of survival (Myers et al., 1989).

Using intralesional BCG, Cho et al. followed a similar protocol as Myers et al. to use PDT on a murine transitional cell carcinoma model (Cho et al., 1992).

Korbelik's group reported results using immuno-adjuvant PDT in 1993 (Korbelik et al., 1993). Initially, the group administered the immunostimulant schizophyllan (SPG), a glucan derived from *Schizophyllum communae*, in a series of intramuscular injections into the hind leg of mice bearing a squamous cell carcinoma solid tumor grown intradermally over the sacral region of the back. PHOTOFRIN®-based PDT was administered either 48 hours after the last SPG treatment or 24 hours before the first SPG injection. SPG therapy before PDT enhanced the effect of PDT on tumor cure whereas immunotherapy after PDT had no effect (Krosl and Korbelik, 1994).

Another study found that administering the macrophage activating factor vitamin $D_3$ binding protein macrophage activating factor (DBPMAF) intraperitoneally and peritumorally in a series starting immediately following PHOTOFRIN®-sensitized PDT enhanced the PDT effect on tumor cures (Korbelik et al., 1997). Later, the group examined the use of BCG and a purified and deproteinized preparation of the mycobacterium cell wall extract (MCWE) that is distributed by Bioniche Inc. (London, Ont. Can.) as REGRESSIN®, combined with PDT sensitized with PHOTOFRIN®, verteporfin, zinc(II)-phthalocyanine (ZnPC), and metatetrahydroxyphenyl-chlorin (mThPC). A single injection of either MCWE or BCG directly beneath the tumor mass and immediately following PDT resulted in enhanced tumor cure rates (Korbelik and Cecic, 1998).

Nordquist et al. (U.S. Pat. No. 5,747,475) disclose that the treatment of primary tumors in a rat model with indocyanine green (ICG) as chromophore and glycated chitosan as an immuno-adjuvant in photothermal therapy. This treatment resulted in some instances of reducing both primary and metastatic tumors as well as some instances of preventing the occurrence of metastatic tumors (see FIGS. 1 and 2 for effects against primary tumors; FIG. 4 for effects against metastatic tumors; and FIG. 5 for prevention of metastatic tumors).

Chen et al. combined glycated chitosan gel (GCG) prepared from crabshell chitin, with indocyanine green (ICG), injected ICG-GCG intratumorally and activated the ICG with thermal laser illumination in a rat metastatic tumor model. The treatment resulted in: a) no tumor response followed by death at 30 days post-treatment; b) reduced tumor burden and extended survival times to 45 days; and c) reduced tumor burden but continued growth of the treated tumor, followed by reduction of both the treated primary and untreated metastasis. Some of the animals in the last group were cured of their tumors and rejected a subsequent challenge with the same tumor cells, indicating that the animals had developed tumor immunity and immunological memory (Chen et al., 1997).

In the above instances, the processes were directed toward discrete or defined, localized tumors. Also, both Nordquist et al. and Chen et al. utilized photothermal mediated cell destruction as opposed to the photochemical mediated PDT discussed below, which does not cause any appreciable heating of the target tissue. Thus experimental combinations of immuno-adjuvants and PDT were attempted with little predictability as to actual efficacy and general application. Even the patent by Nordquist et al. only discloses the results from limited application of this concept with a single combination of one immuno-adjuvant (glycated chitosan) and one chromophore (ICG).

Given that the immune system plays an essential role in tumor destruction and the cytotoxic action of PDT, the present invention relates to a new therapeutic regime combining immunotherapy and PDT for the treatment and prevention of metastatic cancer.

SUMMARY OF THE INVENTION

The invention is directed to the use of photodynamic therapy (PDT) in combination with immuno-adjuvants to treat, prevent, or inhibit the development of any tumor, especially metastatic tumors. This new modality is termed PDV, or photodynamic vaccination, and refers to the combination of PDT and immuno-adjuvants, or immuno-adjuvant PDT, as used herein. In particular, photodynamic methods employing a photosensitizer, such as, but not limited to, a benzoporphyrin derivative (BPD) or a green porphyrin, are used in combination with an immuno-adjuvant against metastatic cancer after diagnosis. Additional applications of the combination are after any primary treatment method against a diagnosed tumor to prevent the onset of as yet undetected dissemination of metastatic tumors or to treat such tumors after their appearance. The instant methods offer the benefit of efficacy against non-localized metastatic tumors either before or after their detection.

Accordingly, in one aspect, the invention is directed to a method to treat metastatic tumors, which method comprises administering to a subject with such tumors an effective amount of a photosensitizer, such as a BPD, in combination with an immuno-adjuvant and irradiating the subject with light absorbed by the photosensitizer. Such methods may be employed against metastatic tumors upon initial diagnosis of cancer in a subject or against metastatic tumors that arise after previous tumor or cancer therapy in the subject.

In another aspect, the invention is directed to a method to prevent or inhibit the development of metastatic tumors by the steps of administering to a subject previously having undergone cancer or tumor therapy, an effective amount of a photosensitizer, such as a BPD, in combination with an immuno-adjuvant and irradiating the subject with light absorbed by the photosensitizer. Such methods are employed even before the detection of metastasis and as such prevent, or reduce the occurrence of, metastatic tumors.

The methods of the present invention specifically are contemplated for the administration of BPDs, such as those described in detail below.

The methods of the present invention may be practiced with any immuno-adjuvant or combination of immunoadjuvants, including those set forth in Appendix A. Particularly preferred immuno-adjuvants are those of microbial or crustacean (chitosan) derived products. These include, but are not limited to, the Ribi Adjuvant System, DETOX™, glycated chitosan, and TiterMax™. The Ribi Adjuvant System and its components are described in issued U.S. Pat. Nos. 4,436,727 and 4,866,034. Preferably, the immuno-adjuvant comprises a mycobacterial cell wall skeleton component (described in U.S. Pat. No. 4,436,727) and a component derived from lipid A of a bacterial lipopolysaccharide. Most preferably, the lipid A component is de-3-O-acylated monophosphoryl lipid A (described in U.S. Pat. No. 4,912,094). Additional adjuvants for use with the present invention include, but are limited to, CFA, BCG, chitosan, and IFA. Delivery of the immuno-adjuvant may be systemic or localized. In an additional embodiment of the invention, administration of the immuno-adjuvant may be repeated after the initial administration of photosensitizer and immuno-adjuvant (PDV).

The present invention further provides compositions formulated for pharmaceutical applications and use in the methods provided. These compositions include, but are not limited to, those useful for treating or preventing or inhibiting the development of metastatic tumors. Such compositions contain an amount of a photosensitizer in combination with an immuno-adjuvant effective to treat, prevent or inhibit development of metastatic tumors when administered to a subject followed by irradiation with light absorbed by the photosensitizer, and a pharmaceutically acceptable carrier or excipient. Compositions individually containing the photosensitizer and immuno-adjuvant for use together as needed are also provided.

The present invention also provides kits that incorporate the features of the invention and makes possible a convenient means of practicing the invention. Kits of the invention comprise one or more photosensitizer and/or immuno-adjuvant as described herein and may also include other materials that facilitate the practice of the invention, such as, but not limited to, instructions, descriptive indicators or labels, and devices relating to photosensitizer, immunoadjuvant, and/or radiation administration. The items comprising the kit may be supplied in the form of individual packages and/or packaged together, as desired by the skilled person.

BRIEF DESCRIPTION OF THE DRAWINGS

The present invention will be more clearly understood by referring to the following drawings, in which.

DETAILED DESCRIPTION OF THE INVENTION

Figure 1:
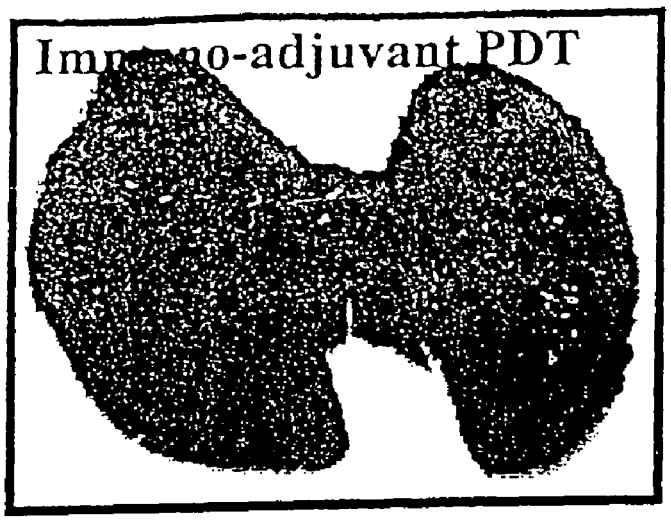
FIG. 1 shows biopsies containing experimental metastases in lungs of animals treated with immuno-adjuvant PDT, PDT only, and untreated controls.
Figure 1:
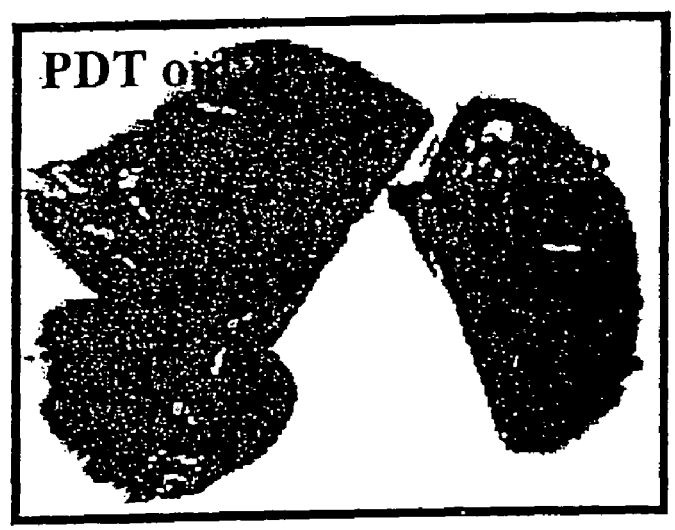
Figure 1:
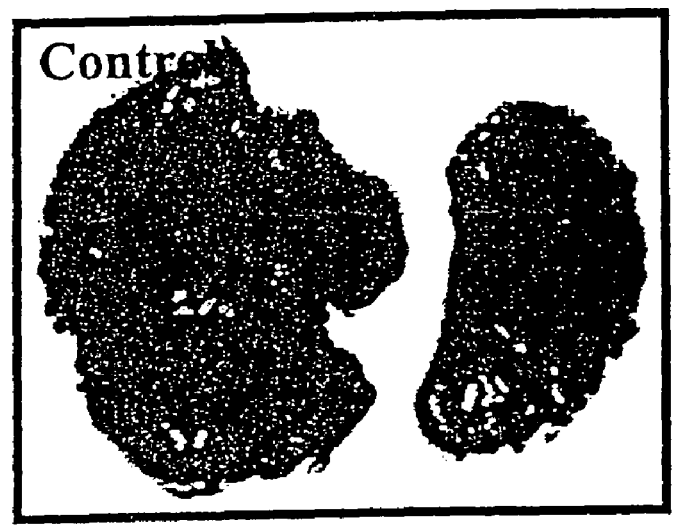

The present invention is directed to a procedure in which immuno-adjuvant photodynamic therapy (PDV) targets tumors, especially metastatic tumors, in some instances even before they are detectable. Thus the invention may be applied against metastatic tumors including, but not limited to, those that originate and/or result in melanoma, lung cancer, breast cancer, colon cancer, and prostate cancer. The invention may also be used in cases of lymphoid tumors that form masses. For treating metastatic tumors that have been newly diagnosed, this treatment may be utilized as a primary therapy against the tumors. For preventing or inhibiting the development of metastatic tumors, this treatment may be used as additional or follow-up therapy after primary therapy against a diagnosed tumor.

Thus following identification of metastatic tumors in a subject, an appropriate photosensitizing compound, preferably BPD-MA, EA6 or B3 as described herein, will be administered to the subject in combination with an immuno-adjuvant. The order of administration of photosensitizer and immuno-adjuvant may vary, with light irradiation following administration of the photosensitizer. The immuno-adjuvant may be administered immediately after light irradiation. Simultaneous activation of the immune system by the immuno-adjuvant and PDT mediated damage to tumor cells, or initiation of immune reactions, may increase the effectiveness of treatment.

After administration, the photosensitizer will localize in tumor cells for photoactivation while the immuno-adjuvant proceeds to activate/potentiate the immune response. Light of appropriate frequency and intensity will be applied using an appropriate light source, thereby activating the photosensitizer to destroy tumor cells and initiate immune responses, possibly by the rapid induction of an inflammatory reaction. Without being bound by theory, PDV may induce systemic cellular and humoral immune responses to tumor cells, including those at other discrete sites as a result of metastasis, that have not undergone photoactivation treatment. PDV treatment of a subject, with light irradiation occurring at a discrete tumor, can thus also treat or prevent "at a distance" discrete tumors of a metastasis without the same photoactivation. This is particularly advantageous in light of the differences between a primary tumor and metastasized tumor lesions. Another non-limiting theory is that the present invention may also serve to help overcome tumor-related immune suppression in late-stage disease.

The formulations and methods of the present invention generally relate to administering a photosensitizer, including pro-drugs such as 5-aminolevulinic acid, porphyrins and porphyrin derivatives e.g. chlorins, bacteriochlorins, isobacteriochlorins phthalocyanine and naphthalocyanines and other tetra- and poly-macrocyclic compounds, and related compounds (e.g. pyropheophorbides) and metal complexes (such as, but not limited by, tin, aluminum, zinc, lutetium) to a subject undergoing the immuno-adjuvant PDT. Further examples of photosensitizers for use in the invention are provided below.

A particularly preferred formulation according to the present invention will satisfy the following general criteria. First, an immuno-adjuvant capable of activating or potentiating the immune response is utilized. Second, a photosensitizer capable of rapid entry into the target tumor cells is used. Third, irradiation with light results in cytotoxicity to target tumor cells. This then results in the generation of immune responses. These criteria do not necessarily reflect a temporal sequence of events.

In one embodiment, the methods of the invention are used against metastatic tumors after initial diagnosis. In another embodiment, the methods of the invention follow removal or eradication of a solid tumor by conventional treatments such as surgery, radiation, chemotherapy or PDT, including immuno-adjuvant PDT. The latter embodiment may be used to prevent or inhibit the development of, metastatic tumors.

In practice of the invention, the immuno-adjuvant may be administered systemically or locally. Moreover, the immuno-adjuvant may be administered before, after or simultaneous with the photosensitizing BPD. This permits the adjuvant-mediated activation/potentiation of immune responses to overlap with PDT mediated damage to tumor cells and any PDT induced immune responses. Preferably, the immuno-adjuvant is administered immediately, or within about a few minutes to about one hour, after photosensitizer or photosensitizer and light administration. After administration of the photosensitizer, sufficient time is permitted to elapse for the compound to be taken up by the tumor cells. This time for uptake may be varied according to various parameters, including but not limited to the photosensitizer administered, the route of administration, the physiology of the subject and of the tumor cells, and the artisan's skill and experience. With green porphyrins, for example, the elapsed time may be from less than about one minute to more than about three hours, preferably from about one minute to about three hours, and more preferably from about 10 to about 60 minutes. The cells, or tissue containing them, then are irradiated at the wavelength of maximum absorbence of the photosensitizer. In the case of BPDs, the wavelength is usually between about 550 and 695 nm, as discussed above. In particular, red light is advantageous because of its relatively lower energy and the resulting lack of toxicity it poses to normal tissue while the tumor cells are destroyed.

In one embodiment of the invention, the immuno-adjuvant may be administered intratumorally with the photosensitizer similarly or systemically administered. In situations where the tumor is relatively accessible, such as, but not limited to, cutaneous or subcutaneous tumors, the immuno-adjuvant and photosensitizer are readily administered. With tumors that are not readily accessible, such as, but not limited to those of the bowel, lung, and prostate, photoactivation of the photosensitizer may require the administration of light via an appropriate device, such as, but not limited to optical fibers and or catheters. These well known devices may also be used to deliver the immuno-adjuvant, either directly or optionally via some injection means. Alternatively, the tumor may be accessed via surgical intervention, whereby the immuno-adjuvant and light may be delivered while the tumor is exposed. This latter approach may be advantageous in situations where surgical intervention is unable to remove all of the tumor, so that any residual tumor cells can be treated by the methods of the invention. Thus the residual tumor is treated via PDV, which may induce systemic cellular and humoral immune responses to treat or prevent "at a distance" other tumor cells.

In a further embodiment of the invention, and subsequent to an initial PDV treatment, the treated subject can be administered additional "booster" amounts of immuno-adjuvant over time to maintain the PDV effect of treating or preventing other tumors. Subsequent administrations of immuno-adjuvant may be with the same or a different adjuvant, and may be by the same or a different route of administration, to that used in the initial PDV. For example, and without limiting the scope of the invention, the initial PDV may have been conducted by intratumoral administration of immuno-adjuvant (such as in the case of tumor access via surgery) with subsequent identical or different immuno-adjuvants administered intravenously.

The compositions and methods of the present invention provide a useful immuno-adjuvant PDT treatment to treat, prevent or inhibit the development of metastatic tumors. The following describes the compositions and formulations of the present invention and their clinical application. Experimental data also are presented and described.

Since adjuvants may exert their activity by stimulating other agents that potentiate the development of an immune response, another aspect of the invention is the use of such agents in combination with PDT. These agents include those that are immunomodulatory in activity and include several cytokines. Examples of cytokines for use in the present invention are IL-12 and IL-18 (where "IL" refers to interleukin), granulocyte-macrophage colony stimulating factor (GM-CSF), and interferon-γ (IFN-γ), which may be administered locally, systemically, or via expression vectors in combination with PDT.

Another approach of the invention is to utilize a cytokine in combination with a factor that acts to promote the growth of hematopoietic progenitors in the presence of a cytokine. FLT3-ligand, isolated and cloned via the corresponding FLT3 receptor [see refs. Rosnet et al. 1991; Matthews et al. 1991; Rasko et al. 1995; Lyman et al. 1993; Lyman et al. 1994] is an example of such a factor. Alone, FLT3-ligand has relatively little activity but in combination acts synergistically with other cytokines including IL-3, IL-6, IL-7, IL-11, IL-12 and colony stimulating factors to promote the growth of hematopoietic progenitors in vitro (Jacobsen et al. 1995). Following the repeated administration of recombinant FLT3-ligand to mice, splenomegaly, hepatomegaly as well as substantial increases in spleen and blood myeloid progenitor activity were observed (Brasel et al. 1996) indicating that FLT3-ligand mediates a mobilisation and expansion of hematopoietic stem cells.

Unexpectedly, mice given multiple FLT3-ligand injections displayed dramatic increases in numbers of functionally mature dendritic cells (DC) in multiple organs (Maraskovsky et al. 1996; Shurin et al. 1997; Steptoe et al. 1997). Bone marrow-derived DC are potent APC that perform a sentinel role for the immune system. These cells are normally present at low numbers within most tissues. Their abundant expression of major histocompatibility complex (MHC) gene products, adhesion and co-stimulatory molecules is a receptor repertoire that serves in the productive activation of naïve and resting T lymphocytes (Steinman 1991; Banchereau et al. 1998). In association with T cells, DC may interact with and activate B cells and thereby regulate the formation of humoral immunity (Banchereau et al. 1998). DC are significant sources of interleukin-12 (IL-12), a pro-inflammatory cytokine that strongly promotes the formation of cellular immunity (Steinman 1991; Banchereau et al. 1998). In the generation of immune responses, DC are many times more effective than other APC types (B cells, macrophages) (Steinman 1991; Banchereau et al. 1998). Relatively few DC are required for the activation of large numbers of T cells. In most tissues, DC are present in an undifferentiated state, inefficient at stimulating T cells. However, these DC are highly efficient at capturing antigen and the signals provided by antigen acquisition promotes a maturation process that yields DC that are highly effective at activating T lymphocytes. DC phagocytose cells dying by apoptosis (programmed cell death), but not by necrosis (unregulated cell death), and can stimulate the expansion of numbers of antigen-specific cytotoxic T cells that recognize antigens contained within apoptotic cells (Morse et al. 1998; DiNicola et al. 1998). In contrast, macrophages are incapable of processing apoptotic cells for the formation of specific cytotoxic T cell immunity (Morse et al. 1998; DiNicola et al. 1998). The capacity of DC to instigate de novo immune responses has lead to their designation as "nature's adjuvant" (Steinman 1991; Banchereau et al. 1998; Young, et al. 1996; Schuler et al. 1997). Treatments that increase DC numbers and/or promote DC activation may ultimately foster specific T cell immunity.

Recent studies indicate that DC can provoke effective anti-tumour immunity in a variety of experimental systems. In mice, effective immunity against solid tumours has been induced by pre-exposure of DC ex vivo to tumour-derived peptides (Zitvogel et al. 1996), crude cell extracts from non-immunogenic tumours (Flamand et al. 1994), tumour cell-derived mRNA (Ashley et al. 1997; Boczkowski et al. 1996), recombinant viral vectors (Song et al. 1997; Specht et al. 1997) or with DC-tumour cell fusions (Gong et al. 1997). Further, it has been demonstrated that DC can stimulate cytotoxic T cell activity against leukemic cells and lymphoma (Choudhury et al. 1997; Choudhury et al. 1999; Fujii et al. 1999; Hsu et al. 1996). DC exposed to tumour lysates or tumour-associated peptides in vitro had a vaccinating effect in human melanoma patients (Nestle et al. 1998). The formation of specific cytotoxic (CD8+) T cell reactivity appears critical for effective anti-tumour immunity (Schuler et al. 1997; Morse et al. 1998; DiNicola et al. 1998).

In cancer, various factors may blunt the development of anti-tumour immunity. This situation may arise from:
1) The action of soluble factors released by tumour cells that functionally impair immune cells.
2) Low or deficient expression of MHC or co-stimulatory molecules by tumour cells.
3) A low capacity of tumour cells to present tumour-specific antigens to T cells.
4) The loss of tumour-related antigens by tumour cell types.
5) Tumour cell expression of receptors (e.g. Fas ligand) that compromise immune cell survival.

DC are a unique immune cell population that is likely derived from a myeloid lineage precursor cell. DC differentiation from bone marrow precursors is driven by the cytokines GM-CSF and TNF-α (Bancheereau et al. 1998). Additional cytokines including IL-4 and c-kit ligand regulate the differentiation and maturation of DC at different developmental stages (Bancheereau et al. 1998). After multiple FLT3-ligand injections, elevated DC numbers were found in immune and non-immune tissues including the spleen, peripheral blood, thymus, liver, lungs, peritoneal cavity, mesenteric lymph nodes and Peyer's patches. These increases in DC numbers were approximately 17-fold in the spleen, 6-fold in the blood and 4-fold in peripheral lymph nodes. Importantly, these FLT3-ligand induced DC were as effective as splenic DC isolated from untreated mice in the induction of antigen-specific T cell responses. FLT3-ligand also modestly increased the number of natural killer (NK) cells in various regions (Shaw et al. 1998) and promoted the activation of NK in vivo by enhancing the interactions between DC and NK cells (Fernandez et al. 1999).

FLT3-ligand treated mice implanted with syngeneic fibrosarcoma tumour cells, exhibited either no development of the tumour or a significantly lower tumour size (Lynch 1998). In vitro, FLT3-ligand had no direct effect upon tumour cell growth (Lynch 1998). FLT3-ligand produces a therapeutic effect against non-immunogenic tumours (Fernandez et al. 1999), murine melanoma (Esche et al. 1998), murine lymphoma (Esche et al. 1998) and limited the spread of metastases to the liver (Peron et al. 1998). The increased availability of DC in tumour-bearing FLT3-ligand-treated subjects may foster the recognition of tumour-associated structures by DC. The interaction of DC with NK cells may simulate NK cell-mediated tumour cell lysis releasing apoptotic or necrotic cell bodies that are taken up, transported, processed and presented by DC to T lymphocytes (Fernandez et al. 1999).

Thus the present invention includes the use of combined PDT/FLT3-ligand anti-cancer therapy. FLT3-ligand is currently available from Immunex (Seattle, Wash.) as MOBIST™, while recombinant human and mouse FLT3-ligand is available commercially from the biological reagent supplier R&D (Minneapolis, Minn.). Based on mouse studies, FLT3-ligand may be administered to effect an increase in peripheral DC numbers. This may be accomplished by a regimen of regular administrations, such as a number of days for higher animals (e.g. humans). Standard PDT could be administered via intravenous injection of a photosensitizer followed later at a pre-determined time with light irradiation. FLT3-ligand administration may be continued for a number of days after PDT.

FLT3-ligand should be administered in a manner that when PDT is applied there is a high availability of DC within the body. When the delivery of PDT is co-ordinated with an FLT3-ligand-induced zenith in DC numbers, the interaction of DC with dying tumour cells would be optimal. This circumstance would provide the patient's immune system the greatest opportunity to generate a specific and effective response to tumour antigens—potentially providing the potential to limit residual and metastatic cancer through immunologic mechanisms.

Yet another aspect of the invention involves a more direct use of dendritic cell (DC) therapy in combination with PDT. Since tumour cells may lack the capacity to directly stimulate T cell responses due to a lack of the appropriate repertoire of accessory structures (MHC, co-stimulatory molecules, etc.) for instigating the responses, the acquisition of tumour cell material by DC could lead to the formation of specific anti-tumour immunity. Thus the use of ex vivo culture systems may circumvent immunosuppressive influences exerted by the tumour and permit the immune sensitization to tumour antigens.

One means of conducting this approach begins with a subject's peripheral blood DC being prepared and cultured in vitro for 24-48 hours with inactivated (optionally by PDT) tumor cells, tumor antigens, and/or any other tumor specific or related factor. These DC, as antigen presenting cells, are re-introduced into the subject, with PDT applied to the subject either before or after the re-introduction.

The Photosensitizers

The preferred photosensitizers (PSs) of the invention include, but are not limited to, naturally occurring or synthetic porphyrins, pyrroles, chlorins, tetrahydrochlorins, pyropheophorphides, purpurins, porphycenes, phenothiaziniums, pheophorbides, bacteriochlorins, isobacteriochlorins, phthalocyanines, napthalocyanines, and expanded pyrrole-based macrocyclic systems such as, sapphyrins and texaphyrins, and derivatives thereof.

Other PSs suitable for use in the present invention include, but are not limited to, angelicins, some biological macromolecules such as lipofuscin; photosystem II reaction centers; and D1-D2-cyt b-559 photosystem II reaction centers, chalcogenapyrillium dyes, chlorins, chlorophylls, coumarins, cyanines, ceratin DNA and related compounds such as adenosine; cytosine; 2'-deoxyguanosine-5'-monophosphate; deoxyribonucleic acid; guanine; 4-thiouridine; 2'-thymidine 5'-monophosphate; thymidylyl(3'-5')-2'-deoxyadenosine; thymidylyl(3'-5')-2'-deoxyguanosine; thymine; and uracil, certain drugs such as adriamycin; afloqualone; amodiaquine dihydrochloride; chloroquine diphosphate; chlorpromazine hydrochloride; daunomycin; daunomycinone; 5-iminodaunomycin; doxycycline; furosemide; gilvocarcin M; gilvocarcin V; hydroxychloroquine sulfate; lumidoxycycline; mefloquine hydrochloride; mequitazine; merbromin (mercurochrome); primaquine diphosphate; quinacrine dihydrochloride; quinine sulfate; and tetracycline hydrochloride, certain flavins and related compounds such as alloxazine; flavin mononucleotide; 3-hydroxyflavone; limichrome; limiflavin;

6-methylalloxazine; 7-methylalloxazine; 8-methylalloxazine; 9-methylalloxazine; 1-methyl limichrome; methyl-2-methoxybenzoate; 5-nitrosalicyclic acid; proflavine; and riboflavin, fullerenes, metalloporphyrins, metallophthalocyanines, methylene blue derivatives, naphthalimides, naphthalocyanines, certain natural compounds such as bis(4-hydroxy-3-methoxyphenyl)-1,6-heptadiene-3,5-dione; 4-(4-hydroxy-3-methoxyphenyl)-3-buten-2-one;
N-formylkynurenine; kynurenic acid; kynurenine; 3-hydroxykynurenine; DL-3-hydroxykynurenine; sanguinarine; berberine; carmane; and 5,7,9(11),22-ergostatetraene-3 β-ol, nile blue derivatives, NSAIDs (nonsteroidal anti-inflammatory drugs), perylenequinones, phenols, pheophorbides, pheophytins, photosensitizer dimers and conjugates, phthalocyanines, porphycenes, porphyrins, psoralens, purpurins, quinones, retinoids, rhodamines, thiophenes, verdins, vitamins and xanthene dyes (Redmond and Gamlin, *Photochem. Photobiol.*, 70(4):391-475 (1999)).

Exemplary angelicins include 3-aceto-angelicin; angelicin; 3,4'-dimethyl angelicin; 4,4'-dimethyl angelicin; 4,5'-dimethyl angelicin; 6,4'-dimethyl angelicin; 6,4-dimethyl angelicin; 4,4',5'-trimethyl angelicin; 4,4',5'-trimethyl-1'-thioangelicin; 4,6,4'-trimethyl-1'-thioangelicin; 4,6,4'-trimethyl angelicin; 4,6,5'-trimethyl-1'-thioangelicin; 6,4,4'-trimethyl angelicin; 6,4',5'-trimethyl angelicin; 4,6,4',5'-tetramethyl-1'-thioangelicin; and 4,6,4',5'-tetramethyl angelicin.

Exemplary chalcogenapyrillium dyes include pyrilium perchlorate, 4,4'-(1,3-propenyl)-bis[2,6-di(1,1-dimethylethyl)]-; pyrilium perchlorate, 2,6-bis(1,1-dimethyl-ethyl)-4-[1-[2,6-bis(1,1'-dimethyl-ethyl)selenopyran-4-ylidene]-3-propenyl-; pyrilium hexofluoro phosphate, 2,6-bis-(1,1'-dimethyl-ethyl)-selenopyran-4-ylidene]-3-propenyl-; pyrilium perchlorate, 2,6-bis(1,1-dimethyl-ethyl)-4-[1-[2,6-bis(1,1-dimethyl-ethyl)telluropyran-4-ylidene]-3-propenyl-; pyrilium hexofluoro phosphate, 2,6-bis(1,1-dimethyl-ethyl)-4-[1-[2,6-bis(1,1-dimethyl-ethyl)telluropyran-4-ylidene]-3-propenyl-; pyrilium perchlorate, 2,6-bis(1,1-dimethyl-ethyl)-4-[1-[2,6-bis(1,1-dimethyl-ethyl)thiapyran-4-ylidene]-3-propenyl]-; selenopyrilium hexofluoro phosphate, 2,6-bis(1,1-dimethyl-ethyl)-4-[1-[2,6-bis(1,1-dimethyl-ethyl)selenopyran-4-ylidene]-3-propenyl]-; selenopyrilium, 2,6-bis(1,1-dimethylethyl)-4-[1-[2,6-bis(1,1-dimethylethyl)selenopyran-4-ylidene]-3-propenyl]-; selenopyrilium percheorate, 2,6-bis(1,1-dimethyl-ethyl)-4-[1-[2,6-bis(1,1-dimethyl-ethyl)-4-[1-[2,6-bis(1,1-dimethyl-ethyl)telluropyran-4-ylidene]-3-propenyl]-; selenopyrilium hexofluoro phosphate, 2,6-bis(1,1-dimethyl-ethyl)-4-[1-[2,6-bis(1,1-dimethyl-ethyl)telluropyran-4-ylidene]-3-propenyl]-; selenopyrilium hexofluoro phosphate, 2,6-bis(1,1-dimethyl-ethyl)-4-[2-[2,6-bis(1,1-dimethyl-ethyl)selenopyran-4-ylidene]-4-(2-butenyl)]-; selenopyrilium hexofluoro phosphate, 2,6-bis(1,1-dimethyl-ethyl)-4-[2-[2,6-bis(1,1-dimethyl-ethyl)selenopyran-4-ylidene]-4-(2-pentenyl)]-; telluropyrilium tetrafluoroborate, 2,6-bis(1,1-dimethylethyl)-4-[1-[2,6-bis(1,1-dimethyl-ethyl)-telluropyran-4-ylidene]-3-propenyl]-; telluropyrilium hexofluoro phosphate, 2,6-bis(1,1-dimethyl-ethyl)-4-[1-[2,6-bis(1,1-dimethyl-ethyl)telluropyran-4-ylidene]-3-propenyl]-; telluropyrilium hexofluoro phosphate, 2,6-bis(1,1-dimethyl-ethyl)-4-[1-[2,6-bis(1,1-dimethyl-ethyl)telluropyran-4-ylidene]ethyl]-; telluropyrilium hexofluoro phosphate, 2,6-bis(1,1-dimethyl-ethyl)-4-[1-[2,6-bis(1,1-dimethyl-ethyl)-telluropyran-4-ylidene]methyl]-; thiopyrilium hexofluoro phosphate, 2,6-bis(1,1-dimethyl-ethyl)-4-[1-[2,6-bis(1,1-dimethyl-ethyl)thiopyran-4-ylidene]-3-propenyl]-; thiopyrilium hexofluoro phosphate, 2,6-bis(1,1-dimethyl-ethyl)-4-[1-[2,6-bis(1,1-dimethyl-ethyl)selenopyran-4-ylidene]-3-propenyl]-; and thiopyrilium hexofluoro phosphate, 2,6-bis(1,1-dimethyl-ethyl)-4-[1-[2,6-bis(1,1-dimethyl-ethyl)telluropyran-4-ylidene]-3-propenyl]-.

Exemplary chlorins dyes include 5-azachlorin dimethyl ester derivative; 5,10,15,20-tetrakis-(m-hydroxyphenyl) bacteriochlorin; benzoporphyrin derivative monoacid ring A; porphine-2,18-dipropanoic acid, 7-[2-dimethyl-amino)-2-oxoethyl]-8-ethylidene-7,8-dihydro-3,7,12,17-tetramethyl, dimethylester; porphine-2,18-dipropanoic acid, 7-[2-dimethyl-amino)-2-oxoethyl]-8-ethylidene-8-ethyl-7,8-dihydro-3,7,12,17-tetramethyl, dimethylester Z; porphine-2,18-dipropanoic acid, 7-[2-dimethyl-amino)-2-oxoethyl]-8-ethylidene-8-ethyl-7,8-dihydro-3,7,12,17-tetramethyl, dimethylester Z ECHL; porphine-2,18-dipropanoic acid, 7-[2-dimethyl-amino)-2-oxoethyl]-8-ethylidene-8-n-heptyl-7,8-dihydro-3,7,12,17-tetramethyl, dimethylester Z; tin (II) porphine-2,18-dipropanoic acid, 7-[2-(dimethylamino-2-oxoethyl]-8-ethylidene-8-n-heptyl-7,8-dihydro-3,7,12,17-tetramethyl, dimethylester Z; chlorin $e_6$; chlorin $e_6$ dimethyl ester; chlorin $e_6$ $k_3$; chlorin $e_6$ monomethyl ester; chlorin $e_6$ $Na_3$; chlorin $p_6$; chlorin $p_6$-trimethylester; chlorin derivative zinc (II) porphine-2,18-dipropanoic acid, 7-[2-(dimethylamino)-2-oxoethyl]-8-ethylidene-8-n-heptyl-7,8-dihydro-3,7,12,17-tetramethyl, dimethylester Z; $13^1$-deoxy-20-formyl-vic-dihydroxy-bacteriochlorin di-tert-butyl aspartate; $13^1$-deoxy-20-formyl-4-keto-bacteriochlorin di-tert-butyl aspartate; di-L-aspartyl chlorin $e_6$; mesochlorin; 5,10,15,20-tetrakis-(m-hydroxyphenyl) chlorin; meta-(tetrahydroxyphenyl)chlorin; methyl-$13^1$-deoxy-20-formyl-4-keto-bacteriochlorin; mono-L-aspartyl chlorin $e_6$; photoprotoporphyrin IX dimethyl ester; phycocyanobilin dimethyl ester; protochlorophyllide a; tin (IV) chlorin $e_6$; tin chlorin $e_6$; tin L-aspartyl chlorin $e_6$; tin octaethyl-benzochlorin; tin (IV) chlorin; zinc chlorin $e_6$; and zinc L-aspartyl chlorin $e_6$.

Exemplary chlorophylls dyes include chlorophyll a; chlorophyll b; oil soluble chlorophyll; bacteriochlorophyll a; bacteriochlorophyll b; bacteriochlorophyll c; bacteriochlorophyll d; protochlorophyll; protochlorophyll a; amphiphilic chlorophyll derivative 1; and amphiphilic chlorophyll derivative 2.

Exemplary coumarins include 3-benzoyl-7-methoxycoumarin; 7-diethylamino-3-thenoylcoumarin; 5,7-dimethoxy-3-(1-naphthoyl) coumarin; 6-methylcoumarin; 2H-selenolo[3,2-g][1]benzopyran-2-one; 2H-selenolo[3,2-g][1]benzothiopyran-2-one; 7H-selenolo[3,2-g][1]benzoselenopyran-7-one; 7H-selenopyrano[3,2-f][1]benzofuran-7-one; 7H-selenopyrano[3,2-f][1]benzo-thiophene-7-one; 2H-thienol[3,2-g][1]benzopyran-2-one; 7H-thienol[3,2-g][1]benzothiopyran-7-one; 7H-thiopyrano[3,2-f][1]benzofuran-7-one; coal tar mixture; khellin; RG 708; RG277; and visnagin.

Exemplary cyanines include benzoselenazole dye; benzoxazole dye; 1,1'-diethyloxacarbocyanine; 1,1'-diethyloxadicarbocyanine; 1,1'-diethylthiacarbocyanine; 3,3'-dialkylthiacarbocyanines (n=2-18); 3,3'-diethylthiacarbocyanine iodide; 3,3'-dihexylselenacarbocyanine; kryptocyanine; MC540 benzoxazole derivative; MC540 quinoline derivative; merocyanine 540; and meso-ethyl, 3,3'-dihexylselenacarbocyanine.

Exemplary fullerenes include $C_{60}$; $C_{70}$; $C_{76}$; dihydrofullerene; 1,9-(4-hydroxy-cyclohexano)-buckminsterfullerene; [1-methyl-succinate-4-methyl-cyclohexadiene-2,3]-buckminster-fullerene; and tetrahydro fullerene.

Exemplary metalloporphyrins include cadmium (II) chlorotexaphyrin nitrate; cadmium (II) meso-diphenyl tetrabenzoporphyrin; cadmium meso-tetra-(4-N-methylpyridyl)-porphine; cadmium (II) texaphyrin; cadmium (II) texaphyrin nitrate; cobalt meso-tetra-(4-N-methylpyridyl)-porphine; cobalt (II) meso(4-sulfonatophenyl)-porphine; copper hematoporphyrin; copper meso-tetra-(4-N-methylpyridyl)-porphine; copper (II) meso(4-sulfonatophenyl)-porphine; Europium (III) dimethyltexaphyrin dihydroxide; gallium tetraphenylporphyrin; iron meso-tetra(4-N-methylpyridyl)-porphine; lutetium (III) tetra(N-methyl-3-pyridyl)-porphyrin chloride; magnesium (II) meso-diphenyl tetrabenzoporphyrin; magnesium tetrabenzoporphyrin; magnesium tetraphenylporphyrin; magnesium (II) meso(4-sulfonatophenyl)-porphine; magnesium (II) texaphyrin hydroxide metalloporphyrin; magnesium meso-tetra-(4-N-methylpyridyl)-porphine; manganese meso-tetra-(4-N-methylpyridyl)-porphine; nickel meso-tetra(4-N-methylpyridyl)-porphine; nickel (II) meso-tetra(4-sulfonatophenyl)-porphine; palladium (II) meso-tetra-(4-N-methylpyridyl)-porphine; palladium meso-tetra-(4-N-methylpyridyl)-porphine; palladium tetraphenylporphyrin; palladium (II) meso(4-sulfonatophenyl)-porphine; platinum (II) meso(4-sulfonatophenyl)-porphine; samarium (II) dimethyltexaphyrin dihydroxide; silver (II) meso(4-sulfonatophenyl)-porphine; tin (IV) protoporphyrin; tin meso-tetra-(4-N-methylpyridyl)-porphine; tin meso-tetra(4-sulfonatophenyl)-porphine; tin (IV) tetrakis(4-sulfonatophenyl) porphyrin dichloride; zinc (II) 15-aza-3,7,12,18-tetramethyl-porphyrinato-13,17-diyl-dipropionic acid-dimethylester; zinc (II) chlorotexaphyrin chloride; zinc coproporphyrin III; zinc (II) 2,11,20,30-tetra-(1,1-dimethyl-ethyl)tetranaphto(2,3-b:2',3'-g:2"3"-1:2'''3'''-q)porphyrazine; zinc (II) 2-(3-pyridyloxy)benzo[b]-10,19,28-tri(1,1-dimethylethyl)trinaphtho[2',3'-g:2"3"1::2''',3'''-q]porphyrazine; zinc (II) 2,18-bis-(3-pyridyloxy)dibenzo[b,l]-10,26-di(1,1-dimethyl-ethyl)dinaphtho[2',3'-g:2''',3'''-q] porphyrazine; zinc (II) 2,9-bis-(3-pyridyloxy)dibenzo[b,g]-17,26-di(1,1-dimethyl-ethyl)dinaphtho[2",3"-1:2''',3'''-q] porphyrazine; zinc (II) 2,9,16-tris-(3-pyridyloxy) tribenzo[b,g,l]-24=(1,1-dimethyl-ethyl)naphtho[2''',3'''-q] porphyrazine; zinc (II) 2,3-bis-(3-pyridyloxy) benzo[b]-10,19,28-tri(1,1-dimethyl-ethyl)trinaphtho[2',3'-g:2",3"1:2''', 3'''-q]porphyrazine; zinc (II) 2,3,18,19-tetrakis-(3-pyridyloxy) dibenzo[b,l]-10,26-di(1,1-dimethyl-ethyl) trinaphtho[2',3'-g:2''',3'''-q]porphyrazine; zinc (II) 2,3,9,10-tetrakis-(3-pyridyloxy) dibenzo[b,g]-17,26-di(1,1-dimethyl-ethyl)dinaphtho[2",3"-1:2''',3'''-q]porphyrazine; zinc (II) 2,3,9,10,16,17-hexakis-(3-pyridyloxy)tribenzo[b,g,l]-24-(1,1-dimethyl-ethyl)naphtho[2''',3'''-q]porphyrazine; zinc (II) 2-(3-N-methyl)pyridyloxy)benzo[b]-10,19,28-tri(1,1-dimethyl-ethyl)trinaphtho[2',3'-g:2",3"1:2''',3'''-q]porphyrazine monoiodide; zinc (II) 2,18-bis-(3-(N-methyl)pyridyloxy) dibenzo[b,l]-10,26-di(1,1-dimethylethyl)dinaphtho[2',3'-g:2''',3'''-q]porphyrazine diiodide; zinc (II) 2,9-bis-(3-(N-methyl)pyridyloxy)dibenzo[b,g]-17,26-di(1,1-dimethylethyl) dinaphtho[2",3"-1:2''',3'''-q]porphyrazine diiodide; zinc (II) 2,9,16-tris-(3-(N-methyl-pyridyloxy)tribenzo[b,g,l]-24-(1,1-dimethylethyl)naphtho[2''',3'''-q]porphyrazine triiodide; zinc (II) 2,3-bis-(3-(N-methyl)pyridyloxy)benzo[b]-10,19,28-tri(1,1-dimethylethyl)trinaphtho[2',3'-g:2",3"-1:2''',3'''-q] porphyrazine diiodide; zinc (II) 2,3,18,19-tetrakis-(3-(N-methyl)pyridyloxy)dibenzo[b,l]-10,26-di(1,1-dimethyl) dinaphtho[2',3'-g:2''',3'''-q]porphyrazine tetraiodide; zinc (II) 2,3,9,10-tetrakis-(3-(N-methyl)pyridyloxy)dibenzo[g,g]-17,26-di(1,1-dimethylethyl)dinaphtho[2",3"-1:2''',3'''-q]porphyrazine tetraiodide; zinc (II) 2,3,9,10,16,17-hexakis-(3-(N-methyl)pyridyloxy)tribenzo[b,g,l]-24-(1,1-dimethylethyl)naphtho[2''',3'''-q]porphyrazine hexaiodide; zinc (II) meso-diphenyl tetrabenzoporphyrin; zinc (II) meso-triphenyl tetrabenzoporphyrin; zinc (II) meso-tetrakis(2,6-dichloro-3-sulfonatophenyl) porphyrin; zinc (II) meso-tetra-(4-N-methylpyridyl)-porphine; zinc (II) 5,10,15,20-meso-tetra(4-octyl-phenylpropynyl)-porphine; zinc porphyrin c; zinc protoporphyrin; zinc protoporphyrin IX; zinc (II) meso-triphenyl-tetrabenzoporphyrin; zinc tetrabenzoporphyrin; zinc (II) tetrabenzoporphyrin; zinc tetranaphthaloporphyrin; zinc tetraphenylporphyrin; zinc (II) 5,10,15,20-tetraphenylporphyrin; zinc (II) meso (4-sulfonatophenyl)-porphine; and zinc (II) texaphyrin chloride.

Exemplary metallophthalocyanines include aluminum mono-(6-carboxy-pentyl-amino-sulfonyl)-trisulfo-phthalocyanine; aluminum di-(6-carboxy-pentyl-amino-sulfonyl)-trisulfophthalocyanine; aluminum (III) octa-n-butoxy phthalocyanine; aluminum phthalocyanine; aluminum (III) phthalocyanine disulfonate; aluminum phthalocyanine disulfonate; aluminum phthalocyanine disulfonate (cis isomer); aluminum phthalocyanine disulfonate (clinical prep.); aluminum phthalocyanine phthalimido-methyl sulfonate; aluminum phthalocyanine sulfonate; aluminum phthalocyanine trisulfonate; aluminum (III) phthalocyanine trisulfonate; aluminum (III) phthalocyanine tetrasulfonate; aluminum phthalocyanine tetrasulfonate; chloroaluminum phthalocyanine; chloroaluminum phthalocyanine sulfonate; chloroaluminum phthalocyanine disulfonate; chloroaluminum phthalocyanine tetrasulfonate; chloroaluminum-t-butyl-phthalocyanine; cobalt phthalocyanine sulfonate; copper phthalocyanine sulfonate; copper (II) tetra-carboxy-phthalocyanine; copper (II)-phthalocyanine; copper t-butyl-phthalocyanine; copper phthalocyanine sulfonate; copper (II) tetrakis-[methylene-thio[(dimethyl-amino)methylidyne]]phthalocyanine tetrachloride; dichlorosilicon phthalocyanine; gallium (III) octa-n-butoxy phthalocyanine; gallium (II) phthalocyanine disulfonate; gallium phthalocyanine disulfonate; gallium phthalocyanine tetrasulfonate-chloride; gallium (II) phthalocyanine tetrasulfonate; gallium phthalocyanine trisulfonate-chloride; gallium (II) phthalocyanine trisulfonate; $GaPcS_1tBu_3$; $GaPcS_2tBu_2$; $GaPcS_3tBu_1$; germanium (IV) octa-n-butoxy phthalocyanine; germanium phthalocyanine derivative; silicon phthalocyanine derivative; germanium (IV) phthalocyanine octakis-alkoxy-derivatives; iron phthalocyanine sulfonate; lead (II) 2,3,9,10,16,17,23,24-octakis(3,6-dioxaheptyloxy) phthalocyanine; magnesium t-butyl-phthalocyanine; nickel (II) 2,3,9,10,16,17,23,24-octakis(3,6-dioxaheptyloxy) phthalocyanine; palladium (II) octa-n-butoxy phthalocyanine; palladium (II) tetra(t-butyl)-phthalocyanine; (diol) (t-butyl)$_3$-phthalocyanato palladium (II); ruthenium(II) dipotassium[bis(triphenyl-phosphine-monosulphonate) phthalocyanine; silicon phthalocyanine bis (tri-n-hexyl-siloxy)-; silicon phthalocyanine bis(tri-phenyl-siloxy)-; $HOSiPcOSi(CH_3)_2(CH_2)_3N(CH_3)_2$; $HOSiPc OSi(CH_3)_2(CH_2)_3N(CH_2CH_3)_2$; $SiPc[OSi(CH_3)_2(CH_2)_3N (CH_3)_2]_2$; $SiPc[OSi(CH_3)_2(CH_2)_3N(CH_2CH_3)(CH_2)_2N (CH_3)_2]_2$; tin (IV) octa-n-butoxy phthalocyanine; vanadium phthalocyanine sulfonate; zinc (I) octa-n-butoxy phthalocyanine; zinc (II) 2,3,9,10,16,17,23,24-octakis(2-ethoxy-ethoxy) phthalocyanine; zinc (II) 2,3,9,10,16,17,23,24-octakis(3,6-dioxaheptyloxy) phthalocyanine; zinc (II) 1,4,8,11,15,18,22,25-octa-n-butoxy-phthalocyanine; zn(II)-phthalocyanine-octabutoxy; zn(II)-phthalocyanine; zinc phthalocyanine; zinc (II) phthalocyanine; zinc phthalocyanine and perdeuterated zinc phthalocyanine; zinc (II) phthalocyanine disulfonate; zinc phthalocyanine disulfonate; zinc phthalocyanine sulfonate; zinc phthalocyanine tetrabromo-; zinc (II) phthalocyanine tetra-t-butyl-; zinc (II) phthalocyanine tetra-(t-butyl)-; zinc phthalocyanine tetracarboxy-; zinc phthalocyanine tetrachloro-; zinc phthalocyanine tetrahydroxyl; zinc phthalocyanine tetraiodo-; zinc ((I) tetrakis-(1, 1-dimethyl-2-phthalimido)ethyl phthalocyanine; zinc (II) tetrakis-(1,1-dimethyl-2-amino)-ethyl-phthalocyanine; zinc (II) phthalocyanine tetrakis(1,1-dimethyl-2-trimethyl ammonium)ethyl tetraiodide; zinc phthalocyanine tetrasulphonate; zinc phthalocyanine tetrasulfonate; zinc (II) phthalocyanine tetrasulfonate; zinc (II) phthalocyanine trisulfonate; zinc phthalocyanine trisulfonate; zinc (II) (t-butyl)$_3$-phthalocyanine diol; zinc tetradibenzobarreleno-octabutoxy-phthalocyanine; zinc (II) 2,9,16,23,-tetrakis-(3-(N-methyl)pyridyloxy)phthalocyanine tetraiodide; and zinc (II) 2,3,9,10,16,17, 23,24-octakis-(3-(N-methyl)pyridyloxy)phthalocyanine complex octaiodide; and zinc (II) 2,3,9,10,16,17,23,24-octakis-(3-pyridyloxy)phthalocyanine.

Exemplary methylene blue derivatives include 1-methyl methylene blue; 1,9-dimethyl methylene blue; methylene blue; methylene blue (16 μM; methylene blue (14 μM); methylene violet; bromomethylene violet; 4-iodomethylene violet; 1,9-dimethyl-3-dimethyl-amino-7-diethyl-amino-phenothiazine; and 1,9-dimethyl-3-diethylamino-7-dibutyl-amino-phenothiazine.

Exemplary naphthalimides blue derivatives include N,N'-bis-(hydroperoxy-2-methoxyethyl)-1,4,5,8-naphthaldiimide; N-(hydroperoxy-2-methoxyethyl)-1,8-naphthalimide; 1,8-naphthalimide; N,N'-bis(2,2-dimethoxyethyl)-1,4,5,8-naphthaldiimide; and N,N'-bis(2,2-dimethylpropyl)-1,4,5,8-naphthaldiimide.

Exemplary naphthalocyanines include aluminum t-butyl-chloronaphthalocyanine; silicon bis(dimethyloctadecylsiloxy) 2,3-naphthalocyanine; silicon bis(dimethyloctadecylsiloxy) naphthalocyanine; silicon bis(dimethylthexylsiloxy) 2,3-naphthalocyanine; silicon bis(dimethylthexylsiloxy) naphthalocyanine; silicon bis(t-butyldimethylsiloxy) 2,3-naphthalocyanine; silicon bis(tert-butyldimethylsiloxy) naphthalocyanine; silicon bis(tri-n-hexylsiloxy) 2,3-naphthalocyanine; silicon bis(tri-n-hexylsiloxy) naphthalocyanine; silicon naphthalocyanine; t-butylnaphthalocyanine; zinc (II) naphthalocyanine; zinc (II) tetraacetyl-amidonaphthalocyanine; zinc (II) tetraminonaphthalocyanine; zinc (II) tetrabenzamidonaphthalocyanine; zinc (II) tetrahexylamidonaphthalocyanine; zinc (II) tetramethoxy-benzamidonaphthalocyanine; zinc (II) tetramethoxynaphthalocyanine; zinc naphthalocyanine tetrasulfonate; and zinc (II) tetradodecylamidonaphthalocyanine.

Exemplary nile blue derivatives include benzo[a]phenothiazinium, 5-amino-9-diethylamino-; benzo[a]phenothiazinium, 5-amino-9-diethylamino-6-iodo-; benzo[a]phenothiazinium, 5-benzylamino-9-diethylamino-; benzo[a]phenoxazinium, 5-amino-6,8-dibromo-9-ethylamino-; benzo[a]phenoxazinium, 5-amino-6,8-diiodo-9-ethylamino-; benzo[a]phenoxazinium, 5-amino-6-bromo-9-diethylamino-; benzo[a]phenoxazinium, 5-amino-9-diethylamino-(nile blue A); benzo[a]phenoxazinium, 5-amino-9-diethylamino-2,6-diiodo-; benzo[a]phenoxazinium, 5-amino-9-diethylamino-2,-iodo; benzo[a]phenoxazinium, 5-amino-9-diethylamino-6-iodo-; benzo[a]phenoxazinium, 5-benzylamino-9-diethylamino-(nile blue 2B); 5-ethylamino-9-diethylamino-benzo[a]phenoselenazinium chloride; 5-ethylamino-9-diethyl-aminobenzo[a]phenothiazinium chloride; and 5-ethylamino-9-diethyl-aminobenzo[a]phenoxazinium chloride.

Exemplary NSAIDs (nonsteroidal anti-inflammatory drugs) include benoxaprofen; carprofen; carprofen dechlorinated (2-(2-carbazolyl) propionic acid); carprofen (3-chloro-carbazole); chlorobenoxaprofen; 2,4-dichlorobenoxaprofen; cinoxacin; ciprofloxacin; decarboxy-ketoprofen; decarboxy-suprofen; decarboxy-benoxaprofen; decarboxy-tiaprofenic acid; enoxacin; fleroxacin; fleroxacin-N-oxide; flumequine; indoprofen; ketoprofen; lomelfloxacin; 2-methyl-4-oxo-2H-1,2-benzothiazine-1,1-dioxide; N-demethyl fleroxacin; nabumetone; nalidixic acid; naproxen; norfloxacin; ofloxacin; pefloxacin; pipemidic acid; piroxicam; suprofen; and tiaprofenic acid.

Exemplary perylenequinones include hypericins such as hypericin; hypericin monobasic sodium salt; di-aluminum hypericin; di-copper hypericin; gadolinium hypericin; terbium hypericin, hypocrellins such as acetoxy hypocrellin A; acetoxy hypocrellin B; acetoxy iso-hypocrellin A; acetoxy iso-hypocrellin B; 3,10-bis[2-(2-aminoethylamino)ethanol] hypocrellin B; 3,10-bis[2-(2-aminoethoxy)ethanol]hypocrellin B; 3,10-bis[4-(2-aminoethyl)morpholine]hypocrellin B; n-butylaminated hypocrellin B; 3,10-bis(butylamine) hypocrellin B; 4,9-bis(butylamine) hypocrellin B; carboxylic acid hypocrellin B; cystamine-hypocrellin B; 5-chloro hypocrellin A or 8-chloro hypocrellin A; 5-chloro hypocrellin B or 8-chloro hypocrellin B; 8-chloro hypocrellin B; 8-chloro hypocrellin A or 5-chloro hypocrellin A; 8-chloro hypocrellin B or 5-chloro hypocrellin B; deacetylated aldehyde hypocrellin B; deacetylated hypocrellin B; deacetylated hypocrellin A; deacylated, aldehyde hypocrellin B; demethylated hypocrellin B; 5,8-dibromo hypocrellin A; 5,8-dibromo hypocrellin B; 5,8-dibromo iso-hypocrellin B; 5,8-dibromo[1,12-CBr=CMeCBr(COMe)]hypocrellin B; 5,8-dibromo[1,12-CHBrC(=CH$_2$)CBr(COMe)]hypocrellin B; 5,8-dibromo[1-CH$_2$COMe, 12-COCOCH$_2$Br-]hypocrellin B; 5,8-dichloro hypocrellin A; 5,8-dichloro hypocrellin B; 5,8-dichlorodeacytylated hypocrellin B; 5,8-diiodo hypocrellin A; 5,8-diiodo hypocrellin B; 5,8-diiodo[1,12-CH=CMeCH (COCH$_2$I$_2$)-]hypocrellin B; 5,8-diiodo[1,12-CH$_2$C(CH$_2$I) =C(COMe)-]hypocrellin B; 2-(N,N-diethylamino) ethylaminated hypocrellin B; 3,10-bis[2-(N,N-diethylamino)-ethylamine]hypocrellin B; 4,9-bis[2-(N,N-diethylamino)-ethylamine]iso-hypocrellin B; dihydro-1,4-thiazine carboxylic acid hypocrellin B; dihydro-1,4-thiazine hypocrellin B; 2-(N,N-dimethylamino) propylamine hypocrellin B; dimethyl-1,3,5,8,10,12-hexamethoxy-4,9-perylenequinone-6,7-diacetate; dimethyl-5,8-dihydroxy-1,3,10,13-tetramethoxy-4,9-perylenequinone-6,7-diacetate; 2,11-dione hypocrellin A; ethanolamine hypocrellin B; ethanolamine iso-hypocrellin B; ethylenediamine hypocrellin B; 11-hydroxy hypocrellin B or 2-hydroxy hypocrellin B; hypocrellin A; hypocrellin B; 5-iodo[1,12-CH$_2$C(CH$_2$I)=C(COMe)-] hypocrellin B; 8-iodo[1,12-CH$_2$C(CH$_2$I)=C(COMe)-] hypocrellin B; 9-methylamino iso-hypocrellin B; 3,10-bis[2-(N,N-methylamino)propylamine]hypocrellin B; 4,9-bis (methylamine iso-hypocrellin B; 14-methylamine iso-hypocrellin B; 4-methylamine iso-hypocrellin B; methoxy hypocrellin A; methoxy hypocrellin B; methoxy iso-hypocrellin A; methoxy iso-hypocrellin B; methylamine hypocrellin B; 2-morpholino ethylaminated hypocrellin B; pentaacetoxy hypocrellin A; PQP derivative; tetraacetoxy hypocrellin B; 5,8,15-tribromo hypocrellin B; calphostin C, Cercosporins such as acetoxy cercosporin; acetoxy iso-cercosporin; aminocercosporin; cercosporin; cercosporin+iso-cercosporin (1/1 molar); diaminocercosporin; dimethylcercosporin; 5,8-dithiophenol cercosporin; iso-cercosporin; methoxycercosporin; methoxy iso-cercosporin; methylcercosporin; noranhydrocercosporin; elsinochrome A; elsinochrome B; phleichrome; and rubellin A.

Exemplary phenols include 2-benzylphenol; 2,2'-dihydroxybiphenyl; 2,5-dihydroxybiphenyl; 2-hydroxybiphenyl; 2-methoxybiphenyl; and 4-hydroxybiphenyl.

Exemplary pheophorbides include pheophorbide a; methyl 13$^1$-deoxy-20-formyl-7,8-vic-dihydro-bacterio-meso-pheophorbide a; methyl-2-(1-dodecyloxyethyl)-2-devinylpyropheophorbide a; methyl-2-(1-heptyl-oxyethyl)-2-devinyl-pyropheophorbide a; methyl-2-(1-hexyl-oxyethyl)-2-devinyl-pyropheophorbide a; methyl-2-(1-methoxy-ethyl)-2-devinyl-pyropheophorbide a; methyl-2-(1-pentyl-oxyethyl)-2-devinyl-pyropheophorbide a; magnesium methyl bacteriopheophorbide d; methyl-bacteriopheophorbide d; and pheophorbide.

Exemplary pheophytins include bacteriopheophytin a; bacteriopheophytin b; bacteriopheophytin c; bacteriopheophytin d; 10-hydroxy pheophytin a; pheophytin; pheophytin a; and protopheophytin.

Exemplary photosensitizer dimers and conjugates include aluminum mono-(6-carboxy-pentyl-amino-sulfonyl)-trisulfophthalocyanine bovine serum albumin conjugate; dihematoporphyrin ether (ester); dihematoporphyrin ether; dihematoporphyrin ether (ester)-chlorin; hematoporphyrin-chlorin ester; hematoporphyrin-low density lipoprotein conjugate; hematoporphyrin-high density lipoprotein conjugate; porphine-2,7,18-tripropanoic acid, 13,13'-(1,3-propanediyl)bis[3,8,12,17-tetramethyl]-; porphine-2,7,18-tripropanoic acid, 13,13'-(1,11-undecanediyl)bis[3,8,12,17-tetramethyl]-; porphine-2,7,18-tripropanoic acid, 13,13'-(1,6-hexanediyl)bis[3,8,12,17-tetramethyl]-; SnCe6-MAb conjugate 1.7:1; SnCe6-MAb conjugate 1.7:1; SnCe6-MAb conjugate 6.8:1; SnCe6-MAb conjugate 11.2:1; SnCe6-MAb conjugate 18.9:1; SnCe6-dextran conjugate 0.9:1; SnCe6-dextran conjugate 3.5:1; SnCe6-dextran conjugate 5.5:1; SnCe6-dextran conjugate 9.9:1; α-terthienyl-bovine serum albumin conjugate (12:1); α-terthienyl-bovine serum albumin conjugate (4:1); and tetraphenylporphine linked to 7-chloroquinoline.

Exemplary phthalocyanines include (diol) (t-butyl)$_3$-phthalocyanine; (t-butyl)$_4$-phthalocyanine; cis-octabutoxy-dibenzo-dinaphtho-porphyrazine; trans-octabutoxy-dibenzo-dinaphtho-porphyrazine; 2,3,9,10,16,17,23,24-octakis2-ethoxyethoxy) phthalocyanine; 2,3,9,10,16,17,23,24-octakis(3,6-dioxaheptyloxy) phthalocyanine; octa-n-butoxy phthalocyanine; phthalocyanine; phthalocyanine sulfonate; phthalocyanine tetrasulphonate; phthalocyanine tetrasulfonate; t-butyl-phthalocyanine; tetra-t-butyl phthalocyanine; and tetradibenzobarreleno-octabutoxy-phthalocyanine.

Exemplary porphycenes include 2,3-($2^3$-carboxy-$2^4$-methoxycarbonyl benzo)-7,12,17-tris(2-methoxyethyl) porphycene; 2-(2-hydroxyethyl)-7,12,17-tri(2-methoxyethyl) porphycene; 2-(2-hydroxyethyl)-7,12,17-tri-n-propyl-porphycene; 2-(2-methoxyethyl)-7,12,17-tri-n-propyl-porphycene; 2,7,12,17-tetrakis(2-methoxyethyl) porphycene; 2,7,12,17-tetrakis(2-methoxyethyl)-9-hydroxy-porphycene; 2,7,12,17-tetrakis(2-methoxyethyl)-9-methoxy-porphycene; 2,7,12,17-tetrakis(2-methoxyethyl)-9-n-hexyloxy-porphycene; 2,7,12,17-tetrakis(2-methoxyethyl)-9-acetoxy-porphycene; 2,7,12,17-tetrakis(2-methoxyethyl)-9-caproyloxy-porphycene; 2,7,12,17-tetrakis(2-methoxyethyl)-9-pelargonyloxy-porphycene; 2,7,12,17-tetrakis(2-methoxyethyl)-9-stearoyloxy-porphycene; 2,7,12,17-tetrakis(2-methoxyethyl)-9-(N-t-butoxycarbonylglycinoxy) porphycene; 2,7,12,17-tetrakis(2-methoxyethyl)-9-[4-((β-apo-7-carotenyl)benzoyloxyl-porphycene; 2,7,12,17-tetrakis(2-methoxyethyl)-9-amino-porphycene; 2,7,12,17-tetrakis(2-methoxyethyl)-9-acetamido-porphycene; 2,7,12,17-tetrakis(2-methoxyethyl)-9-glutaramido-porphycene; 2,7,12,17-tetrakis(2-methoxyethyl)-9-(methyl-glutaramido)-porphycene; 2,7,12,17-tetrakis(2-methoxyethyl)-9-(glutarimido)-porphycene; 2,7,12,17-tetrakis(2-methoxyethyl)-3-(N,N-dimethylaminomethyl)-porphycene; 2,7,12,17-tetrakis(2-methoxyethyl)-3-(N,N-dimethylaminomethyl)-porphycene hydrochloride; 2,7,12,17-tetrakis(2-ethoxyethyl)-porphycene; 2,7,12,17-tetra-n-propyl-porphycene; 2,7,12,17-tetra-n-propyl-9-hydroxy-porphycene; 2,7,12,17-tetra-n-propyl-9-methoxy-porphycene; 2,7,12,17-tetra-n-propyl-9-acetoxy porphycene; 2,7,12,17-tetra-n-propyl-9-(t-butyl glutaroxy)-porphycene; 2,7,12,17-tetra-n-propyl-9-(N-t-butoxycarbonylglycinoxy)-porphycene; 2,7,12,17-tetra-n-propyl-9-(4-N-t-butoxy-carbonyl-butyroxy)-porphycene; 2,7,12,17-tetra-n-propyl-9-amino-porphycene; 2,7,12,17-tetra-n-propyl-9-acetamido-porphycene; 2,7,12,17-tetra-n-propyl-9-glutaramido-porphycene; 2,7,12,17-tetra-n-propyl-9-(methyl glutaramido)-porphycene; 2,7,12,17-tetra-n-propyl-3-(N,N-dimethylaminomethyl) porphycene; 2,7,12,17-tetra-n-propyl-9,10-benzo porphycene; 2,7,12,17-tetra-n-propyl-9-p-benzoyl carboxy-porphycene; 2,7,12,17-tetra-n-propyl-porphycene; 2,7,12,17-tetra-t-butyl-3,6; 13,16-dibenzo-porphycene; 2,7-bis(2-hydroxyethyl)-12,17-di-n-propyl-porphycene; 2,7-bis(2-methoxyethyl)-12,17-di-n-propyl-porphycene; and porphycene.

Exemplary porphyrins include 5-azaprotoporphyrin dimethylester; bis-porphyrin; coproporphyrin III; coproporphyrin III tetramethylester; deuteroporphyrin; deuteroporphyrin IX dimethylester; diformyldeuteroporphyrin IX dimethylester; dodecaphenylporphyrin; hematoporphyrin; hematoporphyrin (8 μM); hematoporphyrin (400 μM); hematoporphyrin (3 μM); hematoporphyrin (18 μM); hematoporphyrin (30 μM); hematoporphyrin (67 μM); hematoporphyrin (150 μM); hematoporphyrin IX; hematoporphyrin monomer; hematoporphyrin dimer; hematoporphyrin derivative; hematoporphyrin derivative (6 μM); hematoporphyrin derivative (200 μM); hematoporphyrin derivative A (20 μM); hematoporphyrin IX dihydrochloride; hematoporphyrin dihydrochloride; hematoporphyrin IX dimethylester; haematoporphyrin IX dimethylester; mesoporphyrin dimethylester; mesoporphyrin IX dimethylester; monoformyl-monovinyl-deuteroporphyrin IX dimethylester; monohydroxyethylvinyl deuteroporphyrin; 5,10,15,20-tetra(o-hydroxyphenyl) porphyrin; 5,10,15,20-tetra(m-hydroxyphenyl) porphyrin; 5,10,15,20-tetrakis-(m-hydroxyphenyl) porphyrin; 5,10,15,20-tetra(p-hydroxyphenyl) porphyrin; 5,10,15,20-tetrakis (3-methoxyphenyl) porphyrin; 5,10,15,20-tetrakis (3,4-dimethoxyphenyl) porphyrin; 5,10,15,20-tetrakis (3,5-dimethoxyphenyl) porphyrin; 5,10,15,20-tetrakis (3,4,5-trimethoxyphenyl) porphyrin; 2,3,7,8,12,13,17,18-octaethyl-5,10,15,20-tetraphenylporphyrin; PHOTOFRIN®; PHOTOFRIN® II; porphyrin c; protoporphyrin; protoporphyrin IX; protoporphyrin dimethylester; protoporphyrin IX dimethylester; protoporphyrin propylaminoethylformamide iodide; protoporphyrin N,N-dimethylaminopropylformamide; protoporphyrin propylaminopropylformamide iodide; protoporphyrin butylformamide; protoporphyrin N,N-dimethylamino-formamide; protoporphyrin formamide; sapphyrin 1 3,12,13,22-tetraethyl-2,7,18,23 tetramethyl sapphyrin-8,17-dipropanol; sapphyrin 2 3,12,13,22-tetraethyl-2,7,18,23 tetramethyl sapphyrin-8-monoglycoside; sapphyrin 3; meso-tetra-(4-N-carboxyphenyl)-porphine; tetra-(3-methoxyphenyl)-porphine; tetra-(3-methoxy-2,4-difluorophenyl)-porphine; 5,10,15,20-tetrakis(4-N-methylpyridyl) porphine; meso-tetra-(4-N-methylpyridyl)-porphine tetrachloride; meso-tetra(4-N-methylpyridyl)-porphine; meso-tetra-(3-N-methylpyridyl)-porphine; meso-tetra-(2-N-methylpyridyl)-porphine; tetra(4-N,N,N-trimethylanilinium) porphine; meso-tetra-(4-N,N,N'-trimethylamino-phenyl) porphine tetrachloride; tetranaphthaloporphyrin; 5,10,15,20-tetraphenylporphyrin; tetraphenylporphyrin; meso-tetra-(4-N-sulfonatophenyl)-porphine; tetraphenylporphine tetrasulfonate; meso-tetra(4-sulfonatophenyl)porphine; tetra(4-sulfonatophenyl)porphine; tetraphenylporphyrin sulfonate; meso-tetra(4-sulfonatophenyl)porphine; tetrakis (4-sulfonatophenyl)porphyrin; meso-tetra(4-sulfonatophenyl)porphine; meso(4-sulfonatophenyl)porphine; meso-tetra(4-sulfonatophenyl)porphine; tetrakis(4-sulfonatophenyl) porphyrin; meso-tetra(4-N-trimethylanilinium)-porphine; uroporphyrin; uroporphyrin I (17 µM); uroporphyrin IX; and uroporphyrin I (18 µM).

Exemplary psoralens include psoralen; 5-methoxypsoralen; 8-methoxypsoralen; 5,8-dimethoxypsoralen; 3-carbethoxypsoralen; 3-carbethoxy-pseudopsoralen; 8-hydroxypsoralen; pseudopsoralen; 4,5',8-trimethylpsoralen; allopsoralen; 3-aceto-allopsoralen; 4,7-dimethyl-allopsoralen; 4,7,4'-trimethyl-allopsoralen; 4,7,5'-trimethyl-allopsoralen; isopseudopsoralen; 3-acetoisopseudopsoralen; 4,5'-dimethyl-isopseudopsoralen; 5',7-dimethyl-isopseudopsoralen; pseudoisopsoralen; 3-acetopseudoisopsoralen; 3/4',5'-trimethyl-aza-psoralen; 4,4',8-trimethyl-5'-amino-methylpsoralen; 4,4',8-trimethyl-phthalamyl-psoralen; 4,5',8-trimethyl-4'-aminomethyl psoralen; 4,5',8-trimethyl-bromopsoralen; 5-nitro-8-methoxypsoralen; 5'-acetyl-4,8-dimethyl-psoralen; 5'-aceto-8-methyl-psoralen; and 5'-aceto-4,8-dimethyl psoralen Exemplary purpurins include octaethylpurpurin; octaethylpurpurin zinc; oxidized octaethylpurpurin; reduced octaethylpurpurin; reduced octaethylpurpurin tin; purpurin 18; purpurin-18; purpurin-18-methyl ester; purpurin; tin ethyl etiopurpurin I; Zn(II) aetio-purpurin ethyl ester; and zinc etiopurpurin.

Exemplary quinones include 1-amino-4,5-dimethoxy anthraquinone; 1,5-diamino-4,8-dimethoxy anthraquinone; 1,8-diamino-4,5-dimethoxy anthraquinone; 2,5-diamino-1, 8-dihydroxy anthraquinone; 2,7-diamino-1,8-dihydroxy anthraquinone; 4,5-diamino-1,8-dihydroxy anthraquinone; mono-methylated 4,5- or 2,7-diamino-1,8-dihydroxy anthraquinone; anthralin (keto form); anthralin; anthralin anion; 1,8-dihydroxy anthraquinone; 1,8-dihydroxy anthraquinone (Chrysazin); 1,2-dihydroxy anthraquinone; 1,2-dihydroxy anthraquinone (Alizarin); 1,4-dihydroxy anthraquinone (Quinizarin); 2,6-dihydroxy anthraquinone; 2,6-dihydroxy anthraquinone (Anthraflavin); 1-hydroxy anthraquinone (Erythroxy-anthraquinone); 2-hydroxy-anthraquinone; 1,2,5,8-tetra-hydroxy anthraquinone (Quinalizarin); 3-methyl-1,6,8-trihydroxy anthraquinone (Emodin); anthraquinone; anthraquinone-2-sulfonic acid; benzoquinone; tetramethyl benzoquinone; hydroquinone; chlorohydroquinone; resorcinol; and 4-chlororesorcinol.

Exemplary retinoids include all-trans retinal; $C_{17}$ aldehyde; $C_{22}$ aldehyde; 11-cis retinal; 13-cis retinal; retinal; and retinal palmitate.

Exemplary rhodamines include 4,5-dibromo-rhodamine methyl ester; 4,5-dibromo-rhodamine n-butyl ester; rhodamine 101 methyl ester; rhodamine 123; rhodamine 6G; rhodamine 6G hexyl ester; tetrabromo-rhodamine 123; and tetramethyl-rhodamine ethyl ester.

Exemplary thiophenes include terthiophenes such as 2,2': 5',2''-terthiophene; 2,2':5',2''-terthiophene-5-carboxamide; 2,2':5',2''-terthiophene-5-carboxylic acid; 2,2':5',2''-terthiophene-5-L-serine ethyl ester; 2,2':5',2''-terthiophene-5-N-isopropynyl-formamide; 5-acetoxymethyl-2,2':5',2''-terthiophene; 5-benzyl-2,2':5',2''-terthiophene-sulphide; 5-benzyl-2,2':5',2''-terthiophene-sulfoxide; 5-benzyl-2,2':5', 2''-terthiophene-sulphone; 5-bromo-2,2':5',2''-terthiophene; 5-(butynyl-3'''-hydroxy)-2,2':5',2''-terthiophene; 5-carboxyl-5''-trimethylsilyl-2,2':5',2''-terthiophene; 5-cyano-2,2':5',2''-terthiophene; 5,5''-dibromo-2,2':5',2''-terthiophene; 5-(1''', 1'''-dibromoethenyl)-2,2':5',2''-terthiophene; 5,5''-dicyano-2, 2':5',2''-terthiophene; 5,5''-diformyl-2,2':5',2''-terthiophene; 5-difluoromethyl-2,2':5',2''-terthiophene; 5,5''-diiodo-2,2':5', 2''-terthiophene; 3,3''-dimethyl-2,2':5',2''-terthiophene; 5,5''-dimethyl-2,2':5',2''-terthiophene; 5-(3''',3'''-dimethylacryloyloxymethyl)-2,2':5',2''-terthiophene; 5,5''-di-(t-butyl)-2,2':5', 2''-terthiophene; 5,5''-dithiomethyl-2,2':5',2''-terthiophene; 3'-ethoxy-2,2':5',2''-terthiophene; ethyl 2,2':5',2''-terthiophene-5-carboxylic acid; 5-formyl-2,2':5',2''-terthiophene; 5-hydroxyethyl-2,2':5',2''-terthiophene; 5-hydroxymethyl-2,2':5',2''-terthiophene; 5-iodo-2,2':5',2''-terthiophene; 5-methoxy-2,2':5',2''-terthiophene; 3'-methoxy-2,2':5',2''-terthiophene; 5-methyl-2,2':5',2''-terthiophene; 5-(3'''-methyl-2'''-butenyl)-2,2':5',2''-terthiophene; methyl 2,2':5',2''-terthiophene-5-[3'''-acrylate]; methyl 2,2':5',2''-terthiophene-5-(3'''-propionate); N-allyl-2, 2':5',2''-terthiophene-5-sulphonamide; N-benzyl-2,2':5',2''-terthiophene-5-sulphonamide; N-butyl-2,2':5',2''-terthiophene-5-sulphonamide; N,N-diethyl-2,2':5',2''-terthiophene-5-sulphonamide; 3,3',4',3''-tetramethyl-2,2':5', 2''-terthiophene; 5-t-butyl-5''-trimethylsilyl-2,2':5',2''-terthiophene; 3'-thiomethyl-2,2':5',2''-terthiophene; 5-thiomethyl-2,2':5',2''-terthiophene; 5-trimethylsilyl-2,2':5', 2''-terthiophene, bithiophenes such as 2,2'-bithiophene; 5-cyano-2,2'-bithiophene; 5-formyl-2,2'-bithiophene; 5-phenyl-2,2'-bithiophene; 5-(propynyl)-2,2'-bithiophene; 5-(hexynyl)-2,2'-bithiophene; 5-(octynyl)-2,2'-bithiophene; 5-(butynyl-4''-hydroxy)-2,2'-bithiophene; 5-(pentynyl-5''-hydroxy)-2,2'-bithiophene; 5-(3'',4''-dihydroxybutynyl)-2, 2'-bithiophene derivative; 5-(ethoxybutynyl)-2,2'-bithiophene derivative, and misclaneous thiophenes such as 2,5-diphenylthiophene; 2,5-di(2-thienyl)furan; pyridine,2,6-bis(2-thienyl)-; pyridine, 2,6-bis(thienyl)-; thiophene, 2-(1-naphthalenyl)-; thiophene, 2-(2-naphthalenyl)-; thiophene, 2,2'-(1,2-phenylene)bis-; thiophene, 2,2'-(1,3-phenylene) bis-; thiophene, 2,2'-(1,4-phenylene)bis-; 2,2':5',2'':5'',2'''-quaterthiophene; α-quaterthienyl; α-tetrathiophene; α-pentathiophene; α-hexathiophene; and α-heptathiophene.

Exemplary verdins include copro (II) verdin trimethyl ester; deuteroverdin methyl ester; mesoverdin methyl ester; and zinc methylpyroverdin.

Exemplary vitamins include ergosterol (provitamin D2); hexamethyl-Co a Co b-dicyano-7-de(carboxymethyl)-7,8-didehydro-cobyrinate (Pyrocobester); pyrocobester; and vitamin D3.

Exemplary xanthene dyes include Eosin B (4',5'-dibromo, 2',7'-dinitro-fluorescein, dianion); eosin Y; eosin Y (2',4',5', 7'-tetrabromo-fluorescein, dianion); eosin (2',4',5',7'-tetrabromo-fluorescein, dianion); eosin (2',4',5',7'-tetrabromo-fluorescein, dianion) methyl ester; eosin (2',4',5',7'-tetrabromo-fluorescein, monoanion) p-isopropylbenzyl ester; eosin derivative (2',7'-dibromo-fluorescein, dianion); eosin derivative (4',5'-dibromo-fluorescein, dianion); eosin derivative (2',7'-dichloro-fluorescein, dianion); eosin derivative (4',5'-dichloro-fluorescein, dianion); eosin derivative (2', 7'-diiodo-fluorescein, dianion); eosin derivative (4',5'-diiodo-fluorescein, dianion); eosin derivative (tribromo-fluorescein, dianion); eosin derivative (2',4',5',7'-tetrachloro-fluorescein, dianion); eosin; eosin dicetylpyridinium chloride ion pair; erythrosin B (2',4',5',7'-tetraiodo-fluorescein, dianion); erythrosin; erythrosin dianion; erythrosin B; fluorescein; fluorescein dianion; phloxin B (2',4',5',7'-tetrabromo-3,4,5,6-tetrachloro-fluorescein, dianion); phloxin B (tetrachloro-tetrabromo-fluorescein); phloxine B; rose bengal (3,4,5,6- tetrachloro-2',4',5',7'-tetraiodofluorescein, dianion); rose bengal; rose bengal dianion; rose bengal O-methyl-methylester; rose bengal 6'-O-acetyl ethyl ester; rose bengal benzyl ester diphenyl-diiodonium salt; rose bengal benzyl ester triethylammonium salt; rose bengal benzyl ester, 2,4,6,-triphenylpyrilium salt; rose bengal benzyl ester, benzyltriphenylphosphonium salt; rose bengal benzyl ester, benzyltriphenyl phosphonium salt; rose bengal benzyl ester, diphenyl-iodonium salt; rose bengal benzyl ester, diphenyl-methylsulfonium salt; rose bengal benzyl ester, diphenyl-methyl-sulfonium salt; rose bengal benzyl ester, triethyl-ammonium salt; rose bengal benzyl ester, triphenyl pyrilium; rose bengal bis (triethyl-ammonium) salt (3,4,5,6-tetrachloro-2',4',5',7'-tetraiodofluorescein, bis (triethyl-ammonium salt); rose bengal bis (triethyl-ammonium) salt; rose bengal bis(benzyl-triphenyl-phosphonium) salt (3,4,5,6-tetrachloro-2',4',5',7'-tetraiodofluorescein, bis(benzyl-triphenyl-phosphonium) salt); rose bengal bis(diphenyl-iodonium) salt (3,4,5,6-tetrachloro-2',4',5',7'-tetraiodofluorescein, bis(diphenyl-iodonium) salt); rose bengal di-cetyl-pyridinium chloride ion pair; rose bengal ethyl ester triethyl ammonium salt; rose bengal ethyl ester triethyl ammonium salt; rose bengal ethyl ester; rose bengal methyl ester; rose bengal octyl ester tri-n-butyl-ammonium salt RB; rose bengal, 6'-O-acetyl-, and ethyl ester.

The above are described in Redmond et al. (Photochemistry and Photobiology, 1999, 70(4):391-475).

Also suitable for the practice of the invention are the class of PS referred to as "green porphyrins." A "green porphyrin" (Gp) is a porphyrin derivative obtained by reacting a porphyrin nucleus with an alkyne in a Diels-Alder type reaction to obtain a mono-hydrobenzoporphyrin. Such resultant macropyrrolic compounds are called benzoporphyrin derivatives (BPDs), which is a synthetic chlorin-like porphyrin with various structural analogues, as shown in U.S. Pat. Nos. 5,283,255, 4,920,143, 4,883,790, and 5,171,749, all of which are hereby incorporated in their entireties as if fully set forth. Non-limiting examples of green porphyrin derivatives are also discussed in U.S. Pat. No. 5,880,145 and related U.S. patent application Ser. No. 09/265,245, both of which are hereby incorporated in their entireties as if fully set forth.

Typically, green porphyrins are selected from a group of tetrapyrrolic porphyrin derivatives obtained by Diels-Alder reactions of acetylene derivatives with protoporphyrin under conditions that promote reaction at only one of the two available conjugated, nonaromatic diene structures present in the protoporphyrin-IX ring systems (rings A and B). Metallated forms of a Gp, in which a metal cation replaces one or two hydrogens in the center of the ring system, may also be used in the practice of the invention. The preparation of the green porphyrin compounds useful in this invention is described in detail in U.S. Pat. No. 5,095,030, which is hereby incorporated by reference as if fully set forth.

Preferably, the BPD is a benzoporphyrin derivative di-acid (BPD-DA), mono-acid ring A (BPD-MA), mono-acid ring B (BPD-MB), or mixtures thereof. These compounds absorb light at about 692 nm wavelength and have improved tissue penetration properties. The compounds of formulas BPD-MA and BPD-MB may be homogeneous, in which only the C ring carbalkoxyethyl or only the D ring carbalkoxyethyl would be hydrolyzed, or may be mixtures of the C and D ring substituent hydrolyzates.

Particularly preferred PSs are BPD-MA, EA6, and B3. BPD-MA, for example, is lipophilic, a potent photosensitizer, and it also appears to be phototoxic to neovascular tissues, tumors and remnant lens epithelial cells. Because of its pharmokinetics, BPD-MA is a preferred PS for use in the instant invention. An optimal BPD for immuno-adjuvant PDT treatment or prevention of metastatic tumors should be rapidly taken up by tumor cells and should be capable of initiating an immune response upon irradiation to act in concert with the immuno-adjuvant.

Of course, one or more PSs and/or one or more immuno-adjuvants may be used in combination. It is preferred that the absorption spectrum of the photosensitizer be in the visible range, typically between 350 nm and 1200 nm, more preferably between 400-900 nm, and even more preferably between 600-900 nm.

BPD-MA is described, for example, in U.S. Pat. No. 5,171,749; EA6 and B3 are described in U.S. Ser. Nos. 09/088,524 and 08/918,840, respectively, all of which are incorporated herein by reference. Preferred green porphyrins have the basic structure:

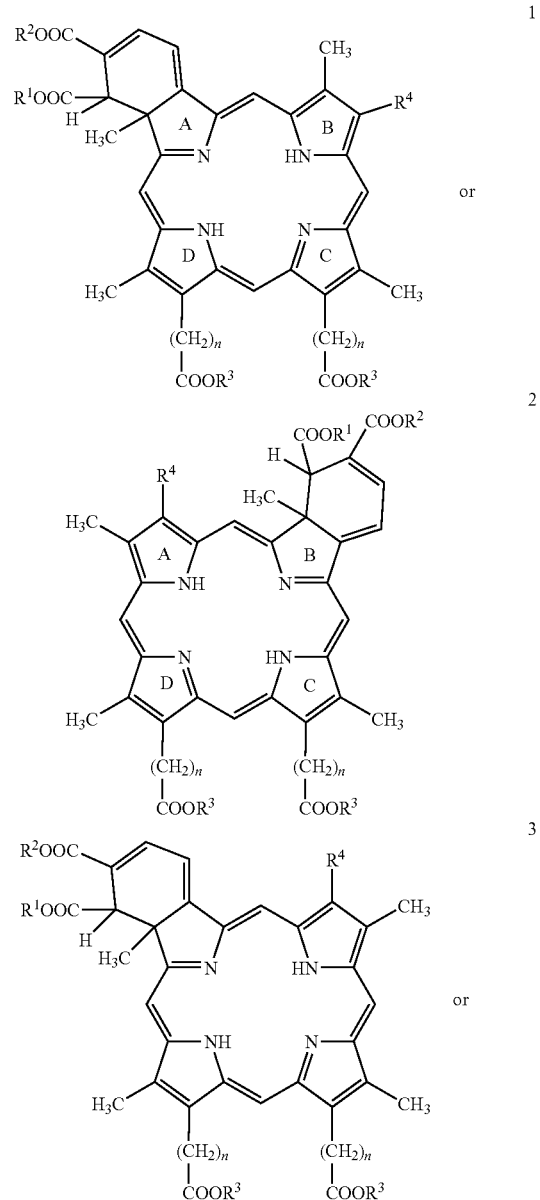

4

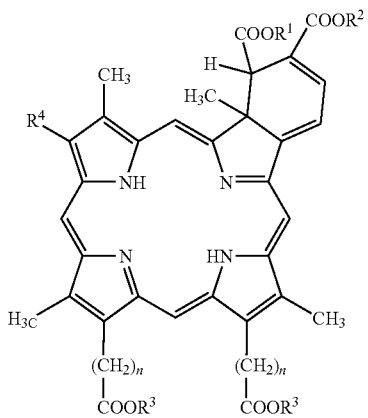

where R⁴ is vinyl or 1-hydroxyethyl and $R^1$, $R^2$, and $R^3$ are H or alkyl or substituted alkyl.

BPD-MA has the structure shown in formula 1 wherein $R^1$ and $R^2$ are methyl, $R^4$ is vinyl and one of $R^3$ is H and the other is methyl. EA6 is of formula 2 wherein $R^1$ and $R^2$ are methyl and both $R^3$ are 2-hydroxyethyl (i.e., the ethylene glycol esters). B3 is of formula 2 wherein $R^1$ is methyl, $R^2$ is H, and both $R^3$ are methyl. In both EA6 and B3, $R^4$ is also vinyl.

Representations of BPD-MA$_C$ and BPD-MA$_D$, which are components of verteporfin, as well as illustrations of A and B ring forms of EA6 and B3, are as follows:

BPD-MA$_C$

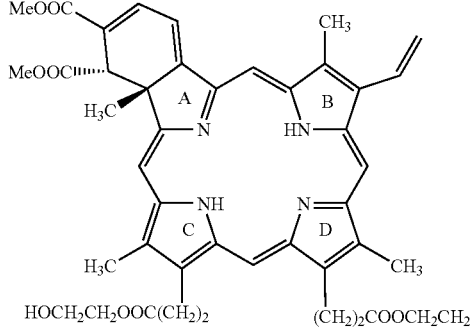

BPD-MA$_D$

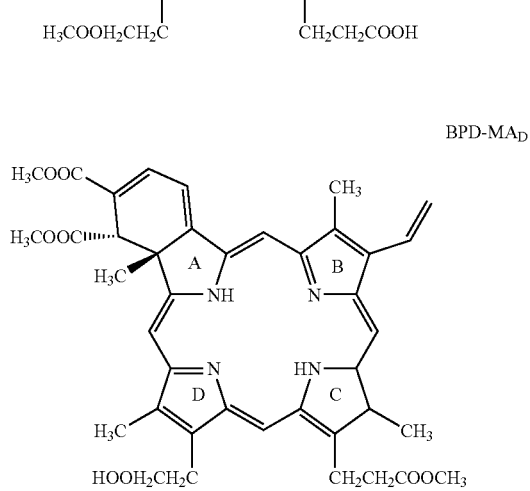

A-EA6

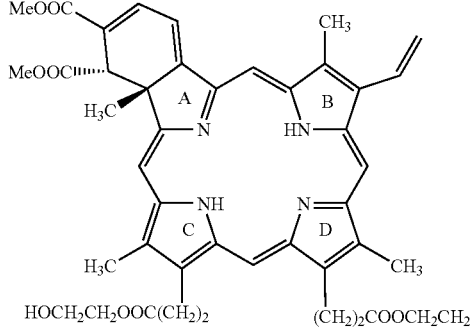

B-EA6

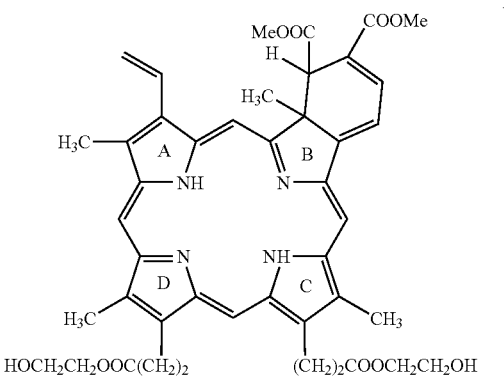

A-B3

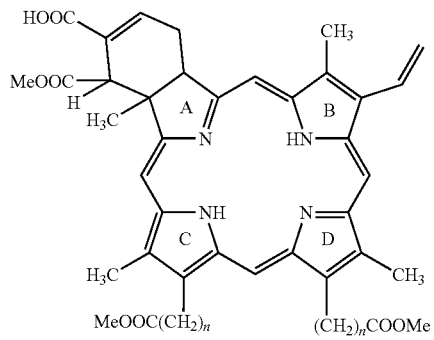

B-B3

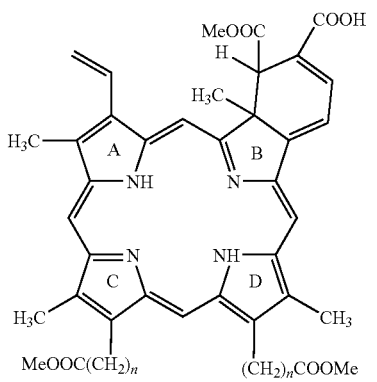

It should be noted that in addition to the above representations of BPD-MA$_C$ and BPD-MA$_D$, there are two other stereoisomers wherein the groups indicated as projecting above and below the plane of the aromatic ring are reversed in their orientation of projection.

Related compounds of formulas 3 and 4 are also useful; in general, $R^4$ will be vinyl or 1-hydroxyethyl and $R^1$, $R^2$, and $R^3$ are H or alkyl or substituted alkyl.

Other non-limiting examples of photosensitizers which may be useful in the invention are photosensitizing Diels-Alder porphyrin derivatives, described in U.S. Pat. No. 5,308,608; porphyrin-like compounds, described in U.S. Pat. Nos. 5,405,957, 5,512675, and 5,726,304; bacteriochlorophyll-A derivatives described in U.S. Pat. Nos. 5,171,741 and 5,173,504; chlorins, isobacteriochlorins and bacteriochlorins, as described in U.S. Pat. No. 5,831,088; meso-monoiodo-substituted and meso substituted tripyrrane, described in U.S. Pat. No. 5,831,088; polypyrrolic macrocycles from meso-substituted tripyrrane compounds, described in U.S. Pat. Nos. 5,703,230, 5,883,246, and 5,919,923; and ethylene glycol esters, described in U.S. Pat. No. 5,929,105. All of the patents cited in this paragraph are hereby incorporated by reference as if fully set forth. Generally any hydrophobic or hydrophilic photosensitizers, which absorb in the ultra-violet, visible and infra-red spectroscopic ranges would be useful for practicing this invention.

Used as part of the present invention, some PSs, such as phthalocyanines, may be used in higher concentrations sufficient to offset their relatively slower uptake by tumor cells.

Dimeric forms of the green porphyrin and dimeric or multimeric forms of green porphyrin/porphyrin combinations may also be used. The dimers and oligomeric compounds of the invention can be prepared using reactions analogous to those for dimerization and oligomerization of porphyrins per se. The green porphyrins or green porphyrin/porphyrin linkages can be made directly, or porphyrins may be coupled, followed by a Diels-Alder reaction of either or both terminal porphyrins to convert them to the corresponding green porphyrins.

Additionally, the PSs used in the invention may be conjugated to various ligands to facilitate targeting to target tumor cells. These ligands include those that are receptor-specific, or immunoglobulins as well as fragments thereof. Preferred ligands include antibodies in general and monoclonal antibodies, as well as immunologically reactive fragments of both.

Formulations

The photosensitizers and immuno-adjuvants of the invention may be formulated into a variety of compositions. These include liposomes, nanoparticles, and pluronic (Poloxamer) containing formulations. Liposomal formulations for porphyrin macrocycle photosensitizers, including green porphyrins, are described in U.S. Pat. No. 6,074,666, which is hereby incorporated in its entirety as if fully set forth. These compositions may also comprise further components, such as conventional delivery vehicles and excipients including isotonising agents, pH regulators, solvents, solubilizers, dyes, gelling agents and thickeners and buffers and combinations thereof. Appropriate formulations and dosages for the administration of immuno-adjuvants are known in the art. Suitable excipients for use with photosensitizers and immuno-adjuvants include water, saline, dextrose, glycerol and the like.

Particularly preferred formulations are those suitable for administration in vivo, such as, but not limited to, sterile, buffered, apyrogenic, and/or isotonic formulations. These include, for example, visible dyes or various enzymes to facilitate the access of a photosensitizing compound to target tumor cells. The immuno-adjuvant may also be administered as a time release formulation.

Typically, the photosensitizer is formulated by mixing it, at an appropriate temperature, e.g., at ambient temperatures, and at appropriate pHs, and the desired degree of purity, with one or more physiologically acceptable carriers, i.e., carriers that are nontoxic at the dosages and concentrations employed. Generally, the pH of the formulation depends mainly on the particular use, and concentration of photosensitizer, but preferably ranges anywhere from about 3 to about 8. Preferably, the photosensitizer is maintained at a pH in the physiological range (e.g., about 6.5 to about 7.5). The presence of salts is not necessary, and, therefore the formulation preferably is not an electrolyte solution. Appropriate nonantigenic ingredients, such as human serum albumin, may optionally be added in amounts that do not interfere with the photosensitizing agent being taken up by lens epithelial cells.

The particular concentration of a given BPD should be adjusted according to its photosensitizing potency. For example, BPD-DA can be used but at about a five-fold higher concentration than that of BPD-MA. Moreover, the BPD may be solubilized in a different manner than by formulation in liposomes. For example, stocks of BPD-MA or any other BPD may be diluted in DMSO (dimethylsulfoxide), polyethylene glycol or any other solvent acceptable for use in the treatment of tumors.

Normally, the adjustment of pH is not required when liposomal BPD-MA is used, as both components have a neutral pH. However, when other solvents than liposomes are used, the pH may require adjustment before mixing the BPD with the other material. Since antioxidants may interfere with the treatment, they should generally should be avoided.

Preparation of dry formulations that are reconstituted immediately before use also are contemplated. The preparation of dry or lyophilized formulations of the compositions of the present invention can also be effected in a known manner, conveniently from the solutions of the invention. The dry formulations of this invention are also storable. By conventional techniques, a solution can be evaporated to dryness under mild conditions, especially after the addition of solvents for azeotropic removal of water, typically a mixture of toluene and ethanol. The residue is thereafter conveniently dried, e.g. for some hours in a drying oven.

Suitable isotonising agents are preferably nonionic isotonising agents such as urea, glycerol, sorbitol, mannitol, aminoethanol or propylene glycol as well as ionic isotonising agents such as sodium chloride. The solutions of this invention will contain the isotonising agent, if present, in an amount sufficient to bring about the formation of an approximately isotonic solution. The expression "an approximately isotonic solution" will be taken to mean in this context a solution that has an osmolarity of about 300 milliosmol (mOsm), conveniently 300+10% mOsm. It should be borne in mind that all components of the solution contribute to the osmolarity. The nonionic isotonising agent, if present, is added in customary amounts, i.e., preferably in amounts of about 1 to about 3.5 percent by weight, preferably in amounts of about 1.5 to 3 percent by weight.

Solubilizers such as Cremophor™ types, preferably Cremophor™ RH 40, or Tween types or other customary solubilisers, may be added to the solutions of the invention in standard amounts.

A further preferred embodiment of the invention relates to a solution comprising a BPD compound, and a partially etherified cyclodextrin, the ether substituents of which are hydroxyethyl, hydroxypropyl or dihydroxypropyl groups, a nonionic isotonising agent, a buffer and an optional solvent. However, appropriate cyclodextrins should be of a size and conformation appropriate for use with the photosensitizing agents disclosed herein.

Summaries of pharmaceutical compositions suitable for use with the instant photosensitizers and immuno-adjuvants are known in the art and are found, for instance, in *Remington's Pharmaceutical Sciences*.

Immuno-Adjuvants

Preferred immuno-adjuvants of the invention contain a bacterial lipid A and a bacterial cell wall skeleton. A non-limiting example for use in the present invention is DETOX™, which contains lipid A from gram-negative bacteria and a Mycobacterium cell wall skeleton. Preferably the immuno-adjuvant is in the form of an emulsion, more preferably a stable oil and water emulsion. Optionally, the immuno-adjuvant is formulated with one or more components selected from a carrier and/or lubricant (such as squalane or squalene); an emulsifier, dispersing agent, and/or surfactant (such as a polysorbate, preferably polysorbate 80, or a lecithin, preferably soy lecithin.

Administration of Photosensitizers and Immuno-Adjuvants

As noted above, the treatment of the present invention is carried out in tissues either maligned with metastatic tumors or susceptible to their occurrence, in an afflicted subject. The photosensitizer and immuno-adjuvant containing preparations of the present invention may be administered systemically or locally and may be used alone or as components of mixtures. Preferred routes of administration are intravenous, subcutaneous, intramuscular, or intraperitoneal injections of the photosensitizers and immuno-adjuvants in conventional or convenient forms. Injection of the adjuvant into a tumor, whether primary or resulting from metastasis, is preferred. Intravenous delivery of photosensitizers is preferred, and intratumor injection may also be used when desired, as in pigmented tumor situations where the dose of PDT would be increased, for example. Oral administration of suitable oral formulations may also be appropriate in those instances where the photosensitizer may be readily administered to the tumor or tumor-prone tissue via this route.

The invention also includes the use of repeat treatments as deemed necessary by a suitable clinician or skilled worker in the field. Preferably, the treatment is repeated from 1 to about 10 times at intervals of about 1 to about 2 weeks. More preferably, the treatment is repeated from 1 to about 5 times, or most preferably for a total of 3 times, at approximately 2 week intervals. The repeat administration of immuno-adjuvant alone as described above may also be conducted at these intervals.

Additionally, if the treatment is to be localized to an area of metastatic tumors suitable for topical formulations, the photosensitizers may be topically administered using standard topical compositions including lotions, suspensions or pastes. The treatment of metastasized tumors may also be performed by the treatment of one tumor lesion during the first PDV treatment followed by another lesion during the second PDV treatment and so forth.

The dose of photosensitizers and immuno-adjuvants can be optimized by the skilled artisan depending on factors such as, but not limited to, the physical delivery system in which it is carried, the individual subject, and the judgment of the skilled practitioner. It should be noted that the various parameters used for effective PDT in the invention are interrelated. Therefore, the dose should also be adjusted with respect to other parameters, for example, fluence, irradiance, duration of the light used in PDT, and time interval between administration of the dose and the therapeutic irradiation. One means of rapidly evaluating parameters for PDT/adjuvant administration is set forth below in Example 4. All of these parameters should be adjusted to produce significant damage to metastatic tumor cells and initiate an immune response without causing significant damage to the surrounding tissue. With photosensitizers, for example, the form of administration, such as in liposomes or when coupled to a target-specific ligand, such as an antibody or an immunologically active fragment thereof, is one factor considered by a skilled artisan.

Depending on the specificity of the preparation, smaller or larger doses of photosensitizers may be needed. For compositions which are highly specific to the target tumors, such as those with the photosensitizer conjugated to a highly specific monoclonal antibody preparation or specific receptor ligand, dosages in the range of 0.01-100 mg/kg are suggested. For compositions which are less specific to the target, dosages of 1-10 mg/kg, may be desirable. For green porphyrins, the use of a dose of about 0.375 mg/kg (equivalent to approximately 14 mg/m$^2$) is preferred. The foregoing ranges are merely suggestive in that the number of variables with regard to an individual treatment regime is large and considerable deviation from these values may be expected. The skilled artisan is free to vary the foregoing concentrations so that the uptake and cellular destruction parameters are consistent with the therapeutic objectives disclosed above.

Systemic administration can also be stated in terms of amount of PS to body surface area of the subject being treated by use of a nomogram that relates body surface area of a human to height and weight.

The time of immuno-adjuvant delivery may be before or after irradiation with light as well as before or after administration of the photosensitizer, although irradiation will occur after administration of the photosensitizer. The immuno-adjuvant may be delivered immediately after irradiation. This may be of particular relevance with immuno-adjuvants that are opaque or otherwise interfere with irradiation.

Without being bound by theory and in instances of BPDs being used as the photosensitizer, irradiation is thought to result in the interaction of BPD in its triplet state with oxygen and other compounds to form reactive intermediates, such as singlet oxygen, which can cause disruption of cellular structures. Possible cellular targets include the cell membrane, mitochondria, lysosomal membranes.

The amount and wavelength of radiation applied is dependent on the nature of the PS used and the effective yield described above. As such, the amount and wavelength should be selected accordingly based on PS selection. For example, the selection of a PS with an activation wavelength in the ultraviolet (UV) region of the electromagnetic spectrum and a low effective yield would lead to the application of UV radiation at a relatively high levels.

In the preferred embodiments of the invention using green porphyrins, the choice of wavelengths is in the visible range, more preferably from about 400 to about 730 nm or from about 650 to about 730, and most preferably at about 690 nm. Irradiation with light in the blue range, such as from about 440 to about 480 nm, may also be used in the practice of the present invention.

With BPDs, an appropriate light source, preferably a laser, laser diode or light emitting diode, in the range of about 550 to about 695 nm, is used to treat target tumor cells. An appropriate and preferred wavelength for such a laser would be 690±12.5 nm at half maximum. Generally, sufficient cell treatment occurs within about 20 minutes, and likely is sufficiently complete within about 10 to about 15 minutes. The light dose administered during the PDT treatment contemplated herein can vary depending on the choice of PS and concentration, but preferably ranges between about 0.25 to 200 J/cm$^2$ or between about 10 to about 150 J/cm$^2$. In preferred embodiments of the invention involving the use of green porphyrins, the light dosage is preferably from about 0.25 to about 0.5, from about 0.5 to 0.75, from about 0.75 to 1.0, from about 1 to 2, from about 2 to 5, from about 5 to 10, from about 10 to 15, from about 15 to 20, from about 20-25, from about 25 to 50, from about 50-75, from about 75 to 100, from 100 to 125, from about 125 to 150, from about 150 to 175, and from about 175 to 200 J/cm$^2$. Most preferred are light doses of about 100, 120, and 180 J/cm$^2$.

Light dosages in the practice of the invention may be delivered at a variety of fluence rates, such as those ranging from about 10 mW/cm$^2$ to about 600 mW/cm$^2$, preferably between about 10 to about 250 mW/cm$^2$. Because the relationship between total light dosage applied and fluency is merely a factor of time (where dosage in Joules equals the fluency in Watts times seconds), the choice of fluence rates depends in part upon the duration of irradiation. For example, a dosage of 120 J/cm$^2$ may be applied at a fluency of 100 mW/cm$^2$ for 20 minutes or a fluency of 200 mW/cm$^2$ for 10 minutes. Increasing irradiance may decrease the exposure times.

Localized delivery of light is preferred, and delivery localized to the tumor is more preferred. Delivery of light prior to photosensitizer activating light is also contemplated to improve penetration of the activating light. For example, irradiation of pigmented melanomas with infrared light before visible red light bleaches the melanin to improve penetration of the red light.

The time of light irradiation after administration of the green porphyrin may be important as one way of maximizing the selectivity of the treatment, thus minimizing damage to structures other than the target tumor cells. Light treatment within about 3 hours before or after application of the photosensitizer should generally be attempted. Alternatively, light treatment may be simultaneous, or nearly simultaneous, with said application.

Kits

The present invention also provides kits that incorporate the features of the invention and makes possible a convenient means of practicing the invention. Kits of the invention comprise one or more PS and/or immuno-adjuvant as described above and may also include other materials that facilitate the practice of the invention, such as, but not limited to, devices for administration of the PS and/or immunoadjuvant or administration of irradiation. The items comprising the kit may be supplied in the form of individual packages and/or packaged together, as desired by the skilled person.

In one embodiment, a kit comprises at least one PS and one immuno-adjuvant in a suitable container. Preferably, the kit contains at least an indication, such as, but not limited to, packaging or a label, identifying the kit, the PS, or the adjuvant as suitable for use in the applications described herein for the present invention and/or at least one instruction relating to the use of the kit, the PS, or the adjuvant in the applications described herein for the present invention. Optionally, the at least one instruction may be part of a larger set of instructions relating to the use of the kit, the PS, or the adjuvant in the applications described herein for the present invention or relating to the use of the kit, the PS, or the adjuvant in the practice of the present invention. Even more preferred are such kits indicated as suitable for use in humans and melanoma or prostate cancer by way the packaging, label, or instructions.

The at least one PS and/or immuno-adjuvant in a kit of the invention may be provided in any form, but preferably, they are provided in a form suitable for immediate use or in a form suitable for use upon reconstitution. As such, the at least one PS and/or immunoadjuvant may be provided in small volumes (e.g. about 100 ml to about 1.0 ml in size) in a suitable formulation as described above or in a suitable formulation for reconstitution (e.g. with sterile water or pyrogen free water or injectable buffer solutions).

The following examples are intended to illustrate but not to limit the invention.

Example 1

Sample Animals and Tumor Model

Male, C57BL/6 mice were obtained from Charles River Canada (Montreal, QC) at 6 to 8 weeks of age. The B 16-F0 and B 16-F1 melanoma cell lines were obtained from the American Type Tissue Collection (ATC™) (Manassas, Va.) and grown as cell cultures in Dulbecco's Modified Eagle Medium (DMEM) (Gibco) supplemented with 10% fetal bovine serum (Sigma). The cells adhered to tissue culture plates, were removed for passage with 0.25% trypsin with 1.0 mM ethylenediaminetetraacetic acid (EDTA) (Gibco), and were cryo-preserved in liquid nitrogen in DMEM plus 40% FBS and 10% DMSO. Mice were injected with 5×10$^5$ tumor cells in a total volume of 50 μL subcutaneously into the shaved, right flank. The tumor size was monitored daily by measuring the diameter with vernier calipers and were treated when the tumors reached approximately 5 mm in diameter. In initial experiments, the B16-F0 and B 16-F1 were characterized with respect to in vivo growth rates and metastatic potential and were found to be identical. Subsequently the B16-F1 cell line was used for all experiments. The injected tumor cells do not result in a representative model of tumor metastasis.

Example 2

Sample Immuno-Adjuvant PDT

PDT treatment of mice bearing the B16-F1 tumor was performed as previously described for the M1 rhabdomyosarcoma mouse tumor (Richter et al., 1987; Richter et al., 1988; Richter et al., 1991). Each mouse was weighed, warmed under infrared light for less than 5 min to dilate the blood vessels, restrained, and injected intravenously (tail vein) with verteporfin at a concentration of 1.0 mg/kg body weight using a 28G needle. Thirty minutes later, animals were restrained and half of the animals were injected intratumorally with 50 μL of TITERMAX™ adjuvant (Sigma) prepared as an emulsion with sterile phosphate buffered saline (PBS) according to the manufacturers specifications. Animals were then exposed to a light dose of 100 J/cm$^2$ in a circular area encompassing the tumor of 1 cm diameter at 688 nm wavelength. The power density was 70 mW/cm$^2$ and resulted in treatment times of 24 min per animal. Following treatment, animals were monitored daily for tumor response.

Example 3

Sample Experimental Metastases

Pulmonary metastases were generated by intravenous injection of tumor cells according to standard methods described by several groups (Chapoval et al., 1998; Lin et al., 1998; Volpert et al., 1998; Wang et al., 1998). Pulmonary metastases were initiated in each group of treated mice, as described in Example 2 above, when the tumor was considered cured. This involved multiple treatments in some of the mice and all test animals were injected intravenously with tumor cells on the same day. Following PDT or immuno-adjuvant PDT animals were monitored for tumor response and if positive, Test (PDT and immuno-adjuvant PDT) and Control (naive) animals were injected with $5\times10^5$ tumor cells in 250 µl PBS via the lateral tail vein. The animals were monitored for tumor recurrence and general health for 14 days after which the animals were sacrificed using $CO_2$ inhalation and their lungs removed. Pulmonary metastases were clearly visible as black tumor colonies against the normal, pink lung tissue.

Results from the above are shown in FIG. 1. The B16 melanoma tumor model is inherently difficult to treat with PDT because of the absorption of light by the black melanin pigment secreted by the tumor cells. However, 10 animals completed the entire course of the experimental procedure. Five animals received PDT alone and of those animals, 3 required repeated PDT treatments to complete the tumor cure. Five animals received immuno-adjuvant PDT and 2 required second treatments with immuno-adjuvant PDT. All of the animals that had been treated with immuno-adjuvant PDT developed between 1 and 7 lung tumors at the time of dissection. One of the animals treated with PDT alone developed 6 lung colonies but the remaining 4 animals developed between 30 and 60 lung colonies. All of the control animals developed 200 to 300 lung colonies but the density of tumor growth made accurate quantification impossible (FIG. 1).

Thus immuno-adjuvant PDT evidently augments tumor immunity that develops during tumor growth and/or following PDT. Although the above example uses pigmented tumors in an experimental metastases approach, the results indicate that the combination of an immuno-adjuvant with PDT can be used for the treatment of metastatic cancer.

Example 4

Rapid Evaluation of PDT/Adjuvant (PDV) Therapy via Lymphocyte Proliferation

In order to assess the potential usefulness of various adjuvants and treatment parameters in PDV, an in vitro lymphocyte proliferation assay was designed and employed in a murine tumor model. The assay measures tumour-specific lymphocyte (tumor immunity) responses from animals treated with PDT and PDT combined with adjuvant (PDV). This permits the rapid evaluation of various PDT/adjuvant administration protocols.

Female C57Bl/6 mice are implanted subcutaneously on the shaved right flank with the Lewis Lung Carcinoma (LLC) cell line. When tumours develop to approximately 5 mm diameter animals are treated with PDT or PDV. PDT is performed by delivering 1.0 mg/kg verteporfin i.v. 30 min prior to illumination of 125 J/cm$^2$ delivered at 70 mW/cm$^2$ (treatment time=29 min, 4 sec). Animals treated with PDV receive a single 50 µl intratumoral injection of adjuvant immediately following illumination. Animals are monitored for general health and re-growth of the tumour following therapy.

Seven to 10 days following therapy, animals are sacrificed and inguinal, axillary, cervical, and periaortic lymph nodes are aseptically removed. A single cell suspension is produced from the lymph nodes and this is cultured in half-area, 96-well tissue culture plates (Corning) in the presence of titrations of freeze/thawed tumour cells and irradiated syngeneic splenocytes depleted of erythrocytes as accessory cells. The cells are cultured in the presence of recombinant interleukin-2 (Sigma), and concanavalin A (ConA) (Sigma) is utilized as a positive control to assess the proliferative capacity of lymphocytes. Following 3 to 5 days of culture, the degree of proliferation is assessed using 3-(4,5-dimethylthiazol-2-yl)-5-(3-carboxymethoxyphenyl)-2-(4-sulfophenyl)-2H-tetrazolium, inner salt (Owen's reagent, MTS, from PROMEGA™), a variation of the MTT assay which produces a soluble formazan product which absorbs light at 490 nm. The degree of proliferation is calculated by comparing the means of at least triplicate test wells to the means of lymphocytes cultured without antigen or mitogen (test mean−MTS background÷control mean−MTS background×100=percent proliferation).

The assays may be performed using the commercial, experimental adjuvant, Ribi Adjuvant System (RAS) (Corixa) or DETOX™ B-SE (Corixa) and alum for comparison.

Figure 2:
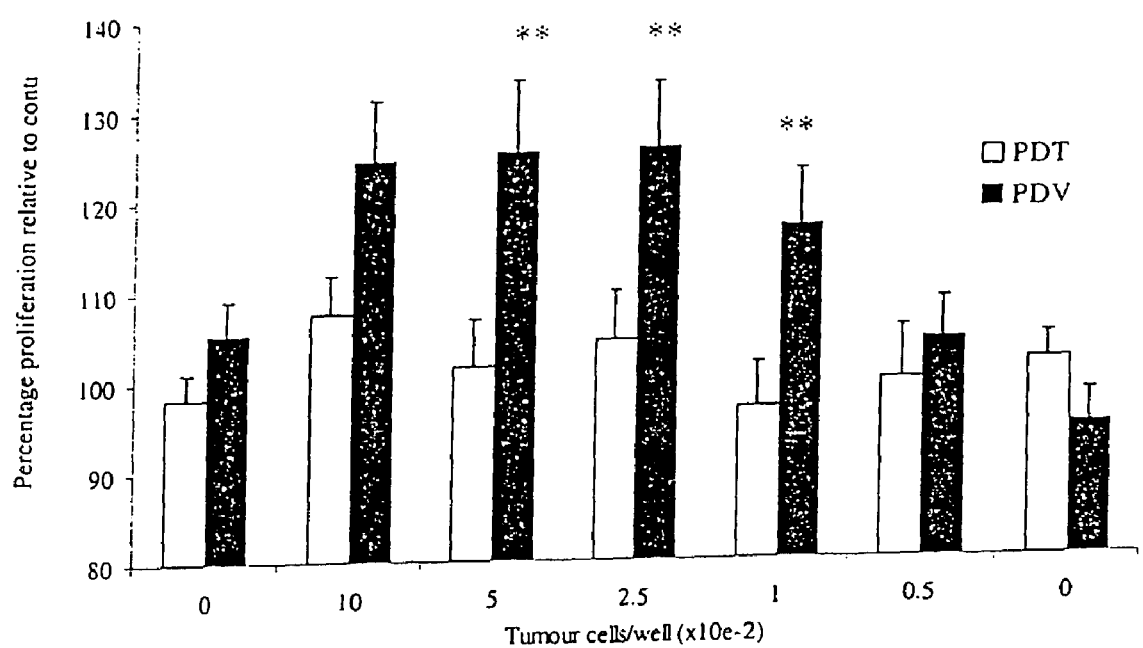
FIG. 2 shows in vitro lymphocyte proliferation in the presence of tumor antigens. See Example 4 below. The lymph nodes of mice bearing the Lewis Lung Carcinoma (LLC) cells were removed 7-10 days following treatment with PDT or PDV. Single cell suspensions of lymphocytes were cultured in the presence of LLC and accessory cells and incubated for 5 days after which proliferation was assessed using MTS.

Of those animals treated with PDV which also responded to ConA (n=7), lymphocytes proliferated to 126±19% (mean±standard deviation) of lymphocytes without antigen (see FIG. 2). Animals treated with PDT alone proliferated to 108±11%. Controls using naïve animals, tumour-bearing animals treated with adjuvant alone, and proliferation in the presence of another syngeneic tumour to test specificity have also been tested.

Example 5

Experimental Protocol for Evaluation of PDT/Adjuvant (PDV) with DETOX™ B-SE

DETOX™ B-SE (Stable Emulsion) (LOT # PD: 071899-575-114) is a 1.0% squalene oil-in-water emulsion containing 145 µg/mL cell wall skeleton (CWS) from *Mycobacterium phlei* and 25 µg/mL monophosphoryl lipid A (MPL) from *Salmonella minnesota* R595 [Corixa Inc.]. DETOX™ B-SE was prepared according to the manufacturer's recommendations. Two concentrations were prepared by diluting DETOX™ B-SE in sterile PBS: 1:10 (7.25 µg/mL CWS, 1.25 µg/mL MPL) or 1:2.5 (29.0 µg/mL CWS, 5.0 µg/mL MPL). Aliquots (50 µL) were drawn into a tuberculin syringe with a 27 gauge needle prior to intratumoral injection.

Mice used in the experiments described below were implanted intradermally with a suspension of $2\times10^4$ M1 (rhabdomyosarcoma) cells on the right flank. Approximately six to ten days after implantation, the site was shaved and tumor growth measured using vernier calipers. Only mice bearing tumors 4-6 mm in diameter were selected for use.

Mice treated with PDT or PDV received 1.0 mg/kg of Verteporfin for Injection (VFI) administered intravenously by tail vein injection. Immediately after injection, the mice were placed in a darkened row of an enclosed, ventilated animal rack (condo unit) for 30 minutes. After 30 minutes, each mouse was secured in a metal holder so that the tumor was centered in a 1.0 cm diameter exposure area. The tumor site was exposed to light from an argon pump dye laser for either 14 minutes, to deliver 75 J/cm$^2$, or 4 minutes and 40 seconds, to deliver 25 J/cm$^2$. The light doses selected were chosen to deliver either a high PDT dose (75 J/cm$^2$) or a low PDT dose (25 J/cm 2). The exposure time in seconds was determined by dividing the light dose (J/cm$^2$) by light Intensity (W/cm$^2$).

Immediately following illumination and while still immobilized in the metal holder, mice received a single intratumoral injection of 50 µL of the 1:10 dilution DETOX™ B-SE, designed to deliver the adjuvant to the center of the tumor mass. Mice in treatment Groups 2 and 5 received 50 µL of 1:2.5 dilution following PDT. See Table 1. Mice in treatment Groups 3 and 6 received PDT treatment, but not adjuvant. Mice in Group 7 remained untreated and were monitored for tumor growth only. Mice in treatment Groups 1 and 4 were treated with 50 µL of 1:10 dilution following PDT.

TABLE 1

Treatment Groups

| Group | | Number of Animals | Drug Dose (mg/kg) | Light Intensity (mW/cm$^2$) | Light Dose (J/cm$^2$) | Exposure Time | Adjuvant Dilution |
|---|---|---|---|---|---|---|---|
| 1 | Optimal PDT + low adjuvant | 10 | 1.0 | 89.2 | 75 | 14 min 0 sec | 1:10 |
| 2 | Optimal PDT + high adjuvant | 10 | 1.0 | 89.2 | 75 | 14 min 0 sec | 1:2.5 |
| 3 | Optimal PDT | 10 | 1.0 | 89.2 | 75 | 14 min 0 sec | 0 |
| 4 | Sub-optimal PDT + low adjuvant | 10 | 1.0 | 89.2 | 25 | 4 min 40 sec | 1:10 |
| 5 | Sub-optimal PDT + high adjuvant | 10 | 1.0 | 89.2 | 25 | 4 min 40 sec | 1:2.5 |
| 6 | Sub-optimal PDT | 10 | 1.0 | 89.2 | 25 | 4 min 40 sec | 0 |
| 7 | Implantation control | 30 | 0 | 0 | 0 | 0 | 0 |

Mice were observed for 20 days, and those found to be tumor-free after 20 days were re-planted intradermally with a suspension of 2×10$^4$ M1 (rhabdomyosarcoma) cells on the right flank. The thirty mice in treatment group 7 were implanted at the same time as those reimplanted on Groups 1-6 to provide a control for the rate of tumor-take. Ten mice were implanted on each of three separate batches of 10 mice to match the days of reimplantation of 1-6.

Example 6

Antitumor Efficacy of PDT/Adjuvant (PDV) with DETOX™ B-SE

Figures 3A, 3B, 3C, 3D:
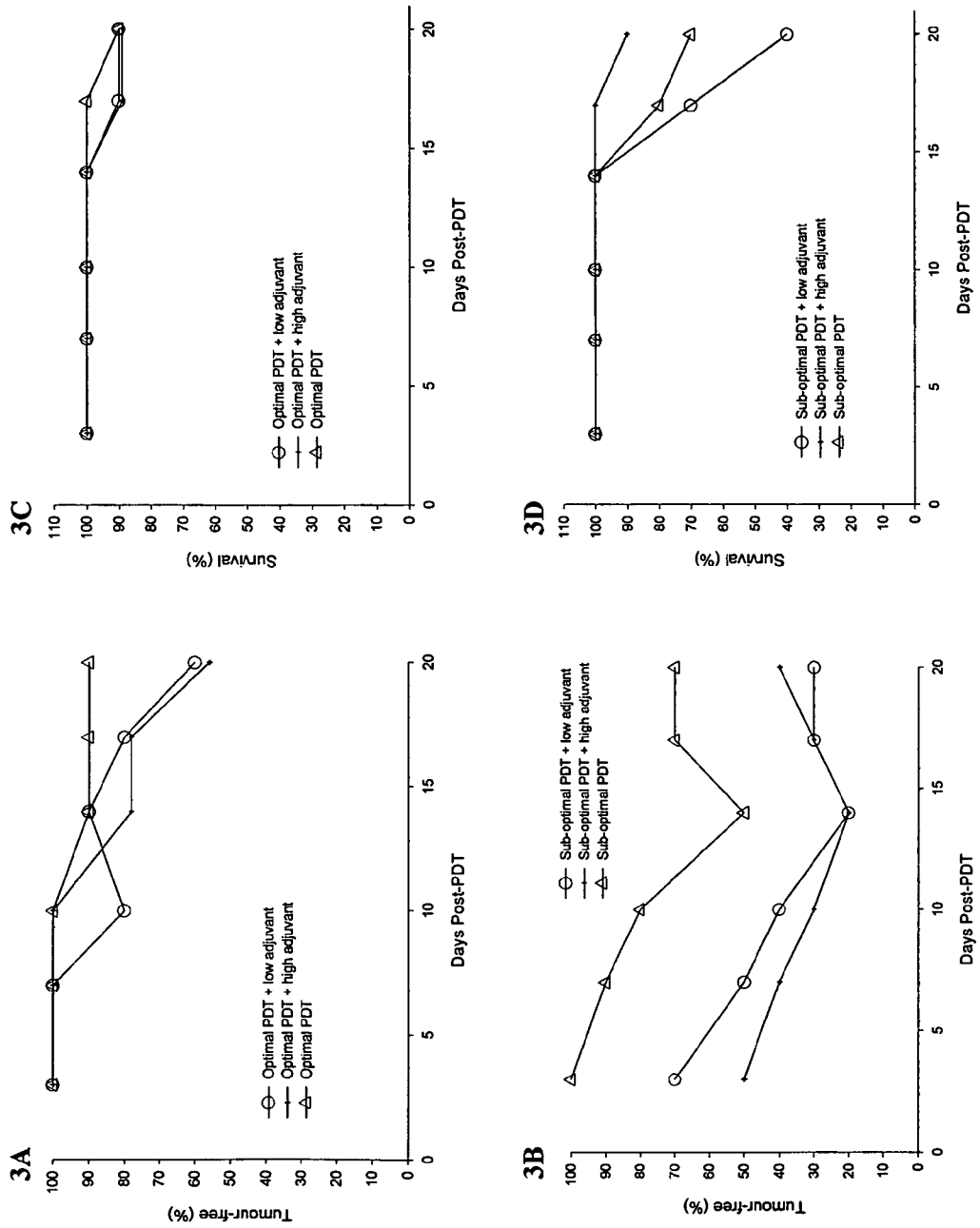
FIG. 3A-3D show tumor responses as described in Examples 5-6 below. Mice were monitored for the presence or absence of a palpable tumor and were sacrificed when tumors reached 1.0 cm in diameter. Graphed values represent the percentage of mice with no evidence of palpable tumors following treatment (3A and 3B), and the percentage of surviving mice whose tumors have not yet reached 1.0 cm in diameter (3C and 3D). Each group contained 10 mice at treatment.

High dose PDT gave virtually complete tumor cure, with 90% of animals being free after 20 days (FIG. 3A, Table 2). The inclusion of DETOX™ B-SE (high and low dose) appeared to give a slight reduction in the number of tumor-free animals with this PDT regime, although the survival at the end of 20 days was identical (FIG. 3C, Table 3).

TABLE 2

Tumor-free mice[a]

| Days Post-PDT | Optimal PDT + low adjuvant | Optimal PDT + high adjuvant | Optimal PDT | Sub-optimal PDT + low adjuvant | Sub-optimal PDT + high adjuvant | Sub-optimal PDT |
|---|---|---|---|---|---|---|
| 3 | 100 | 100 | 100 | 70 | 50 | 100 |
| 7 | 100 | 100 | 100 | 50 | 40 | 90 |
| 10 | 80 | 100[b] | 100 | 40 | 30 | 80 |
| 14 | 90 | 78 | 90 | 20 | 20 | 50 |
| 17 | 80 | 78 | 90 | 30 | 30 | 70 |
| 20 | 60 | 56 | 90 | 30 | 40 | 70 |

[a]Percentage of evaluable mice showing no palpable tumour. Each group contained 10 mice at treatment.
[b]One mouse euthanized, not associated with tumour or therapy. (Excluded from calculations.)

TABLE 3

Survival[a]

| Days Post-PDT | Optimal PDT + low adjuvant | Optimal PDT + high adjuvant | Optimal PDT | Sub-optimal PDT + low adjuvant | Sub-optimal PDT + high adjuvant | Sub-optimal PDT |
|---|---|---|---|---|---|---|
| 3 | 100 | 100 | 100 | 100 | 100 | 100 |
| 7 | 100 | 100 | 100 | 100 | 100 | 100 |
| 10 | 100 | 100[b] | 100 | 100 | 100 | 100 |
| 14 | 100 | 100 | 100 | 100 | 100 | 100 |
| 17 | 90 | 89 | 100 | 70 | 100 | 80 |
| 20 | 90 | 89 | 90 | 40 | 90 | 70 |

[a]Percentage of evaluable mice having a tumour less than 1 cm long and therefore not euthanized. Each group contained 10 mice at treatment.
[b]One mouse euthanized, not associated with tumour or therapy. (Excluded from calculations.)

Low dose PDT also gave effective tumor control with 70% of animals being tumor-days free 20 days after treatment (FIG. 3B, Table 2). Again, addition of DETOX™ B-SE resulted in a slightly lower number of tumor-free animals. Addition of high dose immunoadjuvant resulted in similar survival time relative to PDT alone (FIG. 5D, Table 3) indicating that this therapy is apparently able to prolong the life-span of tumor-bearing animals. Tumor measurements from individual animals treated with low dose PDT combined with high dose adjuvant indicated that 8 out of 10 animals in this group had tumors that were regressing or had regressed completely by Day 20. In the lowdose PDT alone group, 2 out of 10 animals showed similar tumor regression.

Example 7

Protection Against Reimplantation by PDT/Adjuvant (PDV)

Upon reimplantation of tumor into tumor-free mice on Day 20, the tumor-take rate (percentage of re-implanted animals that showed palpable tumor) of mice treated with PDT, with or without immunoadjuvant, was compared with the tumor-take rate in untreated naïve mice. Implantation of naïve mice (Group 7) resulted in 100% tumor take within 10 days (FIG.

Figures 4A, 4B, 4C, 4D:
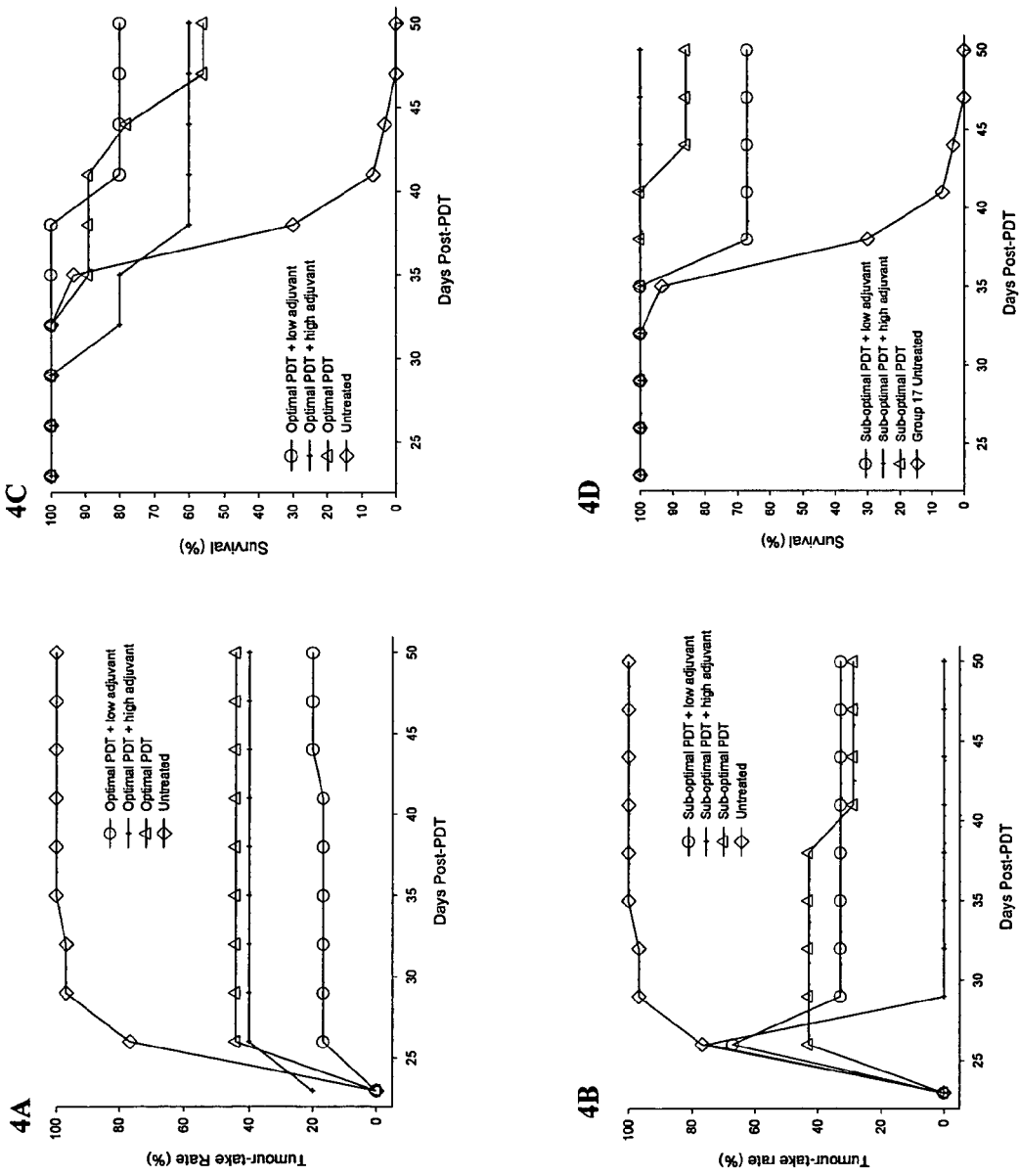
FIG. 4A-4D show tumor growth after reimplantation as described in Example 7 below. Mice were monitored for the presence or absence of a palpable tumor after reimplantation of tumor-free mice and were sacrificed when tumors reached 1.0 cm in diameter. Graphed values represent the percentage of mice with evidence of palpable tumors (tumor take) following reimplantation (4A and 4B), and the percentage of surviving mice whose tumors have not yet reached 1.0 cm in diameter (4C and 4D). Each group contained 10 mice at treatment.

4A, Table 4). High dose PDT gave approximately 60% fewer tumors (n=9), and this percentage was not changed by the addition of high dose immunoadjuvant (n=5). The lower dose of immunoadjuvant combined with high dose PDT gave more protection against rechallenge (20% take rate, n=6). A similar trend was seen in survival to 30 days post reimplantation, where high dose DETOX™-BSE had little or no effect in addition to high dose PDT alone (FIG. 4C, Table 5). The lower immunoadjuvant dose gave more prolonged survival.

TABLE 4

Tumor-take Rate[a]

| Days Post-PDT | Optimal PDT + low adjuvant n = 6 | Optimal PDT + high adjuvant n = 5 | Optimal PDT n = 9 | Sub-optimal PDT + low adjuvant n = 3 | Sub-optimal PDT + high adjuvant n = 4 | Sub-optimal PDT n = 7 | Untreated n = 30 |
|---|---|---|---|---|---|---|---|
| 23 | 0 | 20[c] | 0 | 0 | 0 | 0 | 0 |
| 26 | 17 | 40[c] | 44[d] | 67 | 75 | 43 | 77 |
| 29 | 17 | 40[c] | 44[c] | 33 | 0 | 43 | 97 |
| 32 | 17 | 40[c] | 44[c] | 33 | 0 | 43 | 97 |
| 35 | 17 | 40[c] | 44[c] | 33 | 0 | 43 | 100 |
| 38 | 17 | 40[c] | 44[c] | 33 | 0 | 43 | 100 |
| 41 | 20[b] | 40[c] | 44[c] | 33 | 0 | 29 | 100 |
| 44 | 20 | 40[c] | 44[c] | 33 | 0 | 29 | 100 |
| 47 | 20 | 40[c] | 44[c] | 33 | 0 | 29 | 100 |
| 50 | 20 | 40[c] | 44[c] | 33 | 0 | 29 | 100 |

[a]Percentage of evaluable mice showing no palpable tumour. Each group contained 10 mice at treatment. Untreated group contained 30 mice.
[b]One mouse euthanized, not associated with tumour or therapy. (Excluded from calculations.)
[c]Tumour regrowth was seen on the right flank of one mouse.
[d]Tumour regrowth was seen on the right flank of two mice.

TABLE 5

Survival[a]

| Days Post-PDT | Optimal PDT + low adjuvant n = 6 | Optimal PDT + high adjuvant n = 5 | Optimal PDT n = 9 | Sub-optimal PDT + low adjuvant n = 3 | Sub-optimal PDT + high adjuvant n = 4 | Sub-optimal PDT n = 7 | Untreated n = 30 |
|---|---|---|---|---|---|---|---|
| 23 | 100 | 100 | 100 | 100 | 100 | 100 | 100 |
| 26 | 100 | 100 | 100 | 100 | 100 | 100 | 100 |
| 29 | 100 | 100 | 100 | 100 | 100 | 100 | 100 |
| 32 | 100 | 80[c] | 100 | 100 | 100 | 100 | 100 |
| 35 | 100 | 80 | 89[c] | 93 | 100 | 100 | 93 |
| 38 | 100 | 60 | 89 | 30 | 100 | 100 | 30 |
| 41 | 80[b] | 60 | 89 | 7 | 100 | 100 | 7 |
| 44 | 80 | 60 | 78 | 3 | 100 | 86 | 3 |
| 47 | 80 | 60 | 56 | 0 | 100 | 86 | 0 |
| 50 | 80 | 60 | 56 | 0 | 100 | 86 | 0 |

[a]Percentage of evaluable mice having a tumour less than 1 cm long and therefore not euthanized. Each group contained 10 mice at treatment.
[b]One mouse euthanized, not associated with tumour or therapy. (Excluded from calculations.)
[c]Euthanasia of one mouse due to regrowth on right flank.

Upon rechallenge of mice treated with lose dose PDT, the higher dose of DETOX™-BSE gave the greatest degree of protection (0% take rate at 30 days after tumor reimplantation, n=4). The two other treatment groups allowed approximately 30-40% tumor take (FIG. 4B, Table 4). The higher dose of DETOX™-BSE also gave the longest survival with all reimplanted mice surviving for 30 days past reimplantation (FIG. 4D, Table 5). Low dose PDT alone also gave substantial protection relative to controls and was superior to low dose PDT combined with low-dose adjuvant.

Example 8

Protocol for Metastatic Tumors with Enhanzyn™

This protocol may be used for a variety of metastatic tumors, including metastatic melanoma.

Liposomal verteporfin is injected at a dosage of 14 mg/m$^2$ of body surface area, which is a higher dose than for treating AMD. Alternatively, a PS may be administered by a 10 minute infusion. One to three hours (but preferably 45-75 minutes or one hour) later, diode laser light of about 688±6 nm is applied to a total dosage of about 120-180 J/cm$^2$ to the tumor lesion being treated. Preferably, the dosages are for 120 or 180 J/cm$^2$ and/or at a rate of approximately 200 mW/cm$^2$.

The dosage of the Enhanzyn™ adjuvant, which is injected into the lesion after PDT, provides in the range of about 100-200 μg of the cell wall skeleton component, and about 20-30 μg of the monophosphoryl lipid A component. More preferred is the use of about 145 μg of the cell wall skeleton component, and about 25 μg of the monophosphoryl lipid A component. This procedure is carried out at approximately 2 week intervals. Preferably there are 3 PDV treatments, which are preferably to three different metastasized tumor lesions.

The above is preferably used in subjects with metastatic melanoma, such as those who may be diagnosed as having stage III (metastases to regional lymph nodes) or stage W (metastases in distant sites). The prognosis for stage III metastatic melanoma with two or more lymph nodes positive for tumors is only 15% after 10 years, while for stage W disease, the 5 year survival rate is 6%. With metastatic melanoma, the PDV is preferably administered to cutaneous or subcutaneous lesions with the PDV effect acting on other metastatic lesions "at a distance."

The above may also be modified for application to subjects with any metastatic cancer, including those with, or at risk for developing, metastatic prostate cancer. The present invention is particularly suited to such applications where the metastatic cancer includes one or more cutaneous or subcutaneous lesion that is readily treated with PDV without the need for significant invasive procedures, such as but not limited to, surgery.

Example 9

Protocol for PDV with FLT-3 L or GM-CSF

This protocol is designed to model human disease and may be adapted for use in human subjects with a variety of metastatic tumors, including metastatic melanoma.

Mice implanted with M1 tumour cells are administered FLT-3 L or GM-CSF subcutaneously beginning on day 5 after implantation of the tumour and continuing on a daily basis for 10 days. When the tumours reach 4-6 mm in diameter (approx. day 12), mice will be treated with PDT with A-EA6 or another photosensitizer using sub-optimal light conditions that result in a tumour cure in less than half of the animals. One group of mice will receive the adjuvant Enhanzyn™ on the day of PDT treatment to compare the efficacy of Enhanzyn™ to these cytokines. Mice that have no palpable tumours or appear to be in regression 20 days after PDT will be re-challenged with M1 tumour cells. Preliminary experiments have shown that daily injection of FLT3 L (10 μg) into mice for 10 days dramatically increase the numbers of DC.

The overall protocol uses approximately 40 DBA/2 mice implanted with M1 tumors on day 0 (Group 1, 9 mice; Group 2, 9 mice; Group 3, 12 mice; and Group 4, 10 mice). On day 5, FLT-3 L cytokine treatment begins for Group 1 mice, 10 μg subcutaneously (s.c.) for 10 consecutive days; GM-CSF cytokine treatment begins for Group 2 mice, 10 μg s.c. for 10 consecutive days; and vehicle-alone (PBS) injection of Group 3 mice begins for 10 consecutive days.

On or about day 12, Groups 1, 2 and 3 were treated with PDT when tumors reached a diameter of 4 to 6 mm. This is done over a period of about two days and the treatment protocol timing for the groups of mice will be staggered accordingly. All Groups were PDT treated with A-EA6 at 1.4 μmol/kg, 1.1 mg/kg followed by 15, 25 or 50 J/cm² of light containing 690 nm 30 minutes after drug administration. Group 4 mice were administered Enhanzyn™ (1:2.5 dilution with PBS) via intra-tumoral injection immediately following PDT.

This protocol is summarized in the following graphical representation:

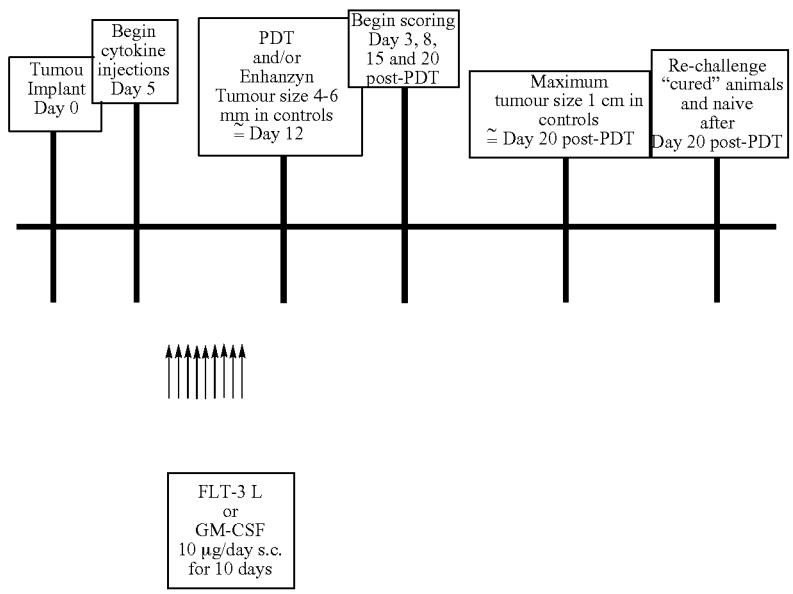

Tumour scoring of the mice will be by assessing the presence of palpable tumour, tumour dimensions, eschar characteristics, erythema and edema according to a standard scoring system, on days 3, 8, 15 and 20 post-PDT. Re-challenges of mice that appear to be in re-mission are with M1 tumour cells on day 20 post-PDT. Naïve mice will be implanted with tumour cells at the same time as mice that are re-challenged.

All references cited herein, including patents, patent applications, and publications, are hereby incorporated by reference in their entireties, whether previously specifically incorporated or not. As used herein, the terms "a", "an", and "any" are each intended to include both the singular and plural forms.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims.

REFERENCES

Albert M L, Pearce S F A, Francisco L M, Sauter B, Roy P, Silverstein R L, Bhardwaj N (1998) Immature dendritic cells phagocytic cells via $\alpha_v\beta_5$ and CD36, and cross-present antigens to cytotoxic T lymphocytes. *J Exp Med* 188 1359-1368.

Albert, M. L., Sauter, B., Bhardwaj, N. (1998) Dendritic cells acquire antigen from apoptotic cells and induce class I-restricted CTLs. *Nature* 392:86-89.

Ashley D M, Faiola B, Nair S, Hale L P, Bigner D D, Gilboa E (1997) Bone marrow-generated dendritic cells pulsed with tumor cell extracts or tumor RNA induce antitumor immunity against central nervous system tumors. *J Exp Med* 186:1177-1182.

Audibert, F. M. and Lise, L. D. (1993) Adjuvants: current status, clinical perspectives and future prospects. *Immunol Today*, 14:281-4.

Banchereau J, Steinman R M *Nature* 392, 245-252 (1998) Dendritic cells and the control of immunity.

Bendandi, M., Gocke, C. D., Kobrin, C. B., Benko, F. A., Sternas, L. A., Pennington, R., Watson, T. M., Reynolds, C. W., Gause, B. L., Duffey, P. L., Jaffe, E. S., Creekmore, S. P., Longo, D. L., and Kwak, L. W. (1999) *Nat Med* 5(10), 1171-7.

Boczkowski D, Nair S K, Snyder D, Gilboa E. (1996) Dendritic cells pulsed with mRNA are potent antigen-presenting cells in vitro and in vivo. *J Exp Med* 184:465-472.

Boon, T., Cerottini, J. C., Van den Eynde, B., van der Bruggen, P. and Van Pel, A. (1994) Tumor antigens recognized by T lymphocytes. *Annual Review of Immunology*, 12:337-365.

Brasel K, McKenna H J, Morrissey P J, Charrier K, Morris A E, Lee C C, Williams D E, Lyman S D (1996) Hematologic effects of flt3 ligand in vivo in mice. *Blood* 88:2004-2012

Burger, U. L., Chang, M. P., Nagoshi, M., Goedegebuure, P. S. and Eberlein, T. J. (1996) Improved in vivo efficacy of tumor-infiltrating lymphocytes after restimulation with irradiated tumor cells in vitro. *Annals of Surgical Oncology*, 3:580-587.

Caux, C., Dezutter-Dambuyant, C., Schmitt, D., and Banchereau, J. (1992) *Nature* 360(6401), 258-61.

Chapoval, A. I., Fuller, J. A., Kremlev, S. G., Kamdar, S. J. and Evans, R. (1998) Combination chemotherapy and IL-15 administration induce permanent tumor regression in a mouse lung tumor model: NK and T cell-mediated effects antagonized by B cells. *J Immunol*, 161:6977-84.

Chen, W. R., Adams, R. L., Carubelli, R. and Nordquist, R. E. (1997) Laser-photosensitizer assisted immunotherapy: a novel modality for cancer treatment. *Cancer Letters*, 115:25-30.

Cho, Y. H., Straight, R. C. and Smith, J. A., Jr. (1992) Effects of photodynamic therapy in combination with intravesical drugs in a murine bladder tumor model. *J Urol*, 147:743-6.

Choudhury A, Gajewski J L, Liang J C, Popat U, Claxton D F, Kliche K.-O, Andreeff M, Champlin R E (1997) Use of dendritic cells for the generation of antileukemic cellular cytotoxicity against Philadelphia chromosome-positive chronic myelogenous leukemia. *Blood* 89:1133-1142.

Choudhury A, Liang J C, Thomas E K, Flores-Romo L, Xie Q S, Agusala K, Sutaria S, Sinha 1, Champlin R E, Claxton D F (1999) Dendritic cells derived in vitro from acute myelogenous leukemia cells stimulate autologous, antileukemic T-cell responses. *Blood* 93:780-786.

Cox, J. C. and Coulter, A. R. (1997) Adjuvants—a classification and review of their modes of action. *Vaccine*, 15:248-56.

Di Nicola M, Anichini A, Mortaini R, Brgni M, Parmiani G, Gianni A M (1998) Human dendritic cells: natural adjuvants in antitumor immunotherapy. *Cytokines Cell Mol Ther* 4:265-273.

Dougherty, T. J., Grindley, G. B., Fiel, R., Weishaupt, K. R. and Boyle, D. G. (1975) Photoradiation therapy. II. Cure of animal tumors with hematoporphyrin and light. *Journal of the National Cancer Institute*, 55:115-119.

Esche C, Subbotin V M, Maliszewski C, Lotze M T, Shurin M R (1998) FLT3 ligand administration inhibits tumor growth in murine melanoma and lymphoma. *Cancer Res* 58:380-383.

Evans, S., Matthews, W., Perry, R., Fraker, D., Norton, J. and Pass, H. I. (1990) Effect of photodynamic therapy on tumor necrosis factor production by murine macrophages. *Journal of the National Cancer Institute*, 82:34-39.

Fernandez N C, Lozier A, Flament C, Ricciardi-Castagnoli P, Bellet D, Suter M, Perricaudet M, Tursz T, Maraskovsky E, Zitvogel L (1999) Dendritic cells directly trigger NK cell functions: cross-talk relevant in innate anti-tumor immune responses in vivo. *Nat Med* 5:405-411.

Fingar, V. H., Wieman, T. J. and Doak, K. W. (1990) Role of thromboxane and prostacyclin release on photodynamic therapy-induced tumor destruction. *Cancer Research*, 50:2599-2603.

Fingar, V. H., Wieman, T. J. and Doak, K. W. (1991) Mechanistic studies of PDT-induced vascular damage: evidence that eicosanoids mediate this process. *International Journal of Radiation Biology*, 60:303-309.

Flamand V, Sornasse T, Thielemans K, Demanet C, Bakkus M, Bazin H, Tielemans F, Leo 0, Urbain J, Moser M (1994) Murine dendritic cells pulsed in vitro with tumor antigen induce tumor resistance in vivo. *Eur J Immunol* 24:605-610.

Fong, L., and Engleman, E. G. (2000) *Annu Rev Immunol* 18, 245-73.

Foster, T. H., Primavera, M. C., Marder, V. J., Hiluf, R. and Sporn, L. A. (1991) Photosensitized release of von Willebrand factor from cultured human endothelial cells. *Cancer Research*, 51:3261-3266.

Fujii S, Fujimoto K, Shimizu K, Ezaki T, Kawano F, Takatsuki K, Kawakita M, Matsuno K (1999) Presentation of tumor antigens by phagocytic dendritic cell clusters generated from human CD34+ hematopoietic progenitor cells: Induction of autologous cytotoxic T lymphocytes against leukemic cells in acute myelogenous leukemia patients. *Cancer Res* 59:2150-2158.

Gajewski, T. F., Renauld, J. C., Van, P. A. and Boon, T. (1995) Costimulation with B7-1, IL-6, and IL-12 is sufficient for primary generation of murine antitumor cytolytic T lymphocytes in vitro. *Journal of Immunology*, 154:5637-5648.

Gollnick, S. O., Liu, X., Owczarczak, B., Musser, D. A. and Henderson, B. W. (1997) Altered expression of interleukin 6 and interleukin 10 as a result of photodynamic therapy in vivo. *Cancer Res*, 57:3904-9.

Gong J, Chen D, Kashiwaba M, Kufe D (1997) Induction of antitumor activity by immunization with fusions of dendritic and carcinoma cells. *Nat Med* 3:558-561.

Gore, M. and Riches, P. (1996) The history of immunotherapy. In Gore, M. and Riches, P. (eds.), *Immunotherapy in cancer*. John Wiley & Sons, Chichester, pp. 1-9.

Granville, D. J., Levy, J. G. and Hunt, D. W. (1998) Photodynamic treatment with benzoporphyrin derivative monoacid ring A produces protein tyrosine phosphorylation events and DNA fragmentation in murine P815 cells. *Photochem Photobiol*, 67:358-62.

Gupta, R. K. and Siber, G. R. (1995) Adjuvants for human vaccines—current status, problems and future prospects. *Vaccine*, 13:1263-76.

Henderson, B. W. and Donovan, J. M. (1989) Release of prostaglandin E2 from cells by photodynamic treatment in vitro. *Cancer Research*, 49:6896-6900.

Henderson, B. W. and Dougherty, T. J. (1992) How does photodynamic therapy work? *Photochemistry and Photobiology*, 55:145-157.

Henderson, B. W., Waldow, S. W., Mang, T. S., Potter, W. R., Malone, P. B. and Dougherty, T. J. (1985) Tumor destruction and kinetics of tumor cell death in two experimental mouse tumors following photodynamic therapy. *Cancer Research*, 45:572-576.

Hewitt, H. B., Blake, E. R. and Walder, A. S. (1976) A critique of the evidence for active host defence against cancer, based on personal studies of 27 murine tumours of spontaneous origin. *British Journal of Cancer*, 33:241-259.

Hewitt, H. (1979) A critical examination of the foundations of immunotherapy for cancer. *Clinical Radiology*, 30:361-369.

Hsu F J, Benike C, Fagnoni F, Liles T M, Czerwinski D, Taidi B, Engleman E G, Levy R (1996) Vaccination of patients with B-cell lymphoma using autologous antigen-pulsed dendritic cells. *Nat Med* 2:52-58.

Jacobsen S E, Okkenhaug C, Myklebust J, Veiby O P, Lyman S D (1995) The FLT3 ligand potently and directly stimulates the growth and expansion of primitive murine bone marrow progenitor cells in vitro: synergistic interactions with interleukin (IL) 11, IL-12, and other hematopoietic growth factors. *J Exp Med* 181:1357-1363.

Jaffee, E. M. and Pardoll, D. M. (1996) Murine tumor antigens: is it worth the search? *Current Opinion in Immunology*, 8:622-627.

Kick G, Messer, Goetz, Plewig, Kind P: Photodynamic therapy induces expression of interleukin 6 by activation of AP-1 but not NF-κB DNA binding. *Cancer Res* (1995) 55:2373-2379.

Korbelik, M., Krosl, G. and Chaplin, D. J. (1993) Can PDT be potentiated by immunotherapy. *Proc. SPIE*, 1616:192-198.

Korbelik M, Krosl G: Enhanced macrophage cytotoxicity against tumor cells treated with photodynamic therapy. *Photochem Photobiol* (1994) 60:497-502.

Korbelik M: Induction of tumor immunity by photodynamic therapy. *J Clin Laser Med Surg* (1996) 14:329-334.

Korbelik, M., Krosl, G., Krosl, J. and Dougherty, G. J. (1996) The role of host lymphoid populations in the response of mouse EMT6 tumor to photodynamic therapy. *Cancer Research*, 56:5647-5652.

Korbelik, M., Naraparaju, V. R. and Yamamoto, N. (1997) Macrophage-directed immunotherapy as adjuvant to photodynamic therapy of cancer. *British Journal of Cancer*, 75:202-7.

Korbelik, M. and Cecic, I. (1998) Enhancement of tumour response to photodynamic therapy by adjuvant mycobacterium cell-wall treatment. *J Photochem Photobiol B*, 44:151-8.

Krosl G, Korbelik M, Dougherty G J: Induction of immune cell infiltration into murine SCCVII tumour by photofrin-based photodynamic therapy. *Br J Cancer* (1995) 71:549-555.

Krosl G, Korbelik M, Krosl J, Dougherty G J: Potentiation of photodynamic therapy-elicited antitumor response by localized treatment with granulocyte-macrophage colony-stimulating factor. *Cancer Res* (1996) 56:3281-3286.

Krosl, G. and Korbelik, M. (1994) Potentiation of photodynamic therapy by immunotherapy: the effect of schizophyllan (SPG). *Cancer Letters*, 84:43-49.

Krosl, G., Korbelik, M. and Dougherty, G. J. (1995) Induction of immune cell infiltration into murine SCCVII tumour by PHOTOFRIN®-based photodynamic therapy. *British Journal of Cancer*, 71:549-555.

Lin, P., Buxton, J. A., Acheson, A., Radziejewski, C., Maisonpierre, P. C., Yancopoulos, G. D., Channon, K. M., Hale, L. P., Dewhirst, M. W., George, S. E. and Peters, K. G. (1998) Antiangiogenic gene therapy targeting the endothelium-specific receptor tyrosine kinase Tie2. *Proc Natl Acad Sci USA*, 95:8829-34.

Liotta, L. A. and Stetler-Stevenson, W. G. (1989) Principles of molecular cell biology of cancer: Cancer metastasis. In DeVita Jr., V. T., Hellman, S. and Rosenberg, S. A. (eds.), *Cancer: Principles and Practice*. J.B. Lippincott Company, Philadelphia, Vol. 1, pp. 98-115.

Lyman S D, James L, Johnson L, Brasel K, de Vries P, Escobar S S, Downey H, Splett R R, Beckmann M P, McKenna H J (1994) Cloning of the human homologue of the murine flt3 ligand: a growth factor for early hematopoietic progenitor cells. *Blood* 83:2795-2801.

Lyman S D, James L, Vanden Bos T, de Vries P, Brasel K, Gliniak B, Hollingsworth L T, Picha K S, McKenna H J, Splett R R, Fletcher F A, Maraskovsky E, Farrah T, Foxworthe D, Willams D E, Beckman M P (1993) Molecular cloning of a ligand for the flt3/flk-2 tyrosine kinase receptor: a proliferative factor for primitive hematopoietic cells. *Cell* 75:1157-1167.

Lynch D H (1998) Induction of dendritic cells (DC) by Flt3 Ligand (FL) promotes the generation of tumor-specific immune responses in vivo. *Crit Rev Immunol* 18:99-107.

Lynch, D. H., Andreasen, A., Maraskovsky, E., Whitmore, J., Miller, R. E., and Schuh, J. C. (1997) *Nat Med* 3(6), 625-31.

Malawer, M. M. and Delaney, T. F. (1989) Treatment of metastatic cancer.

Maraskovsky E, Brasel K, Teepe M, Roux E R, Lyman S D, Shortman K, McKenna H J (1996) Dramatic increase in the numbers of functionally mature dendritic cells in Flt3 ligand-treated mice: multiple dendritic cell subpopulations identified. *J Exp Med* 184:1953-1962.

Maraskovsky, E., Daro, E., Roux, E., Teepe, M., Maliszewski, C. R., Hoek, J., Caron, D., Lebsack, M. E., and McKenna, H. J. (2000) *Blood* 96(3), 878-84.

Matthews W, Jordan C T, Wiegand G W, Pardoll D, Lemischka I R (1991) A receptor tyrosine kinase specific to hematopoietic stem and progenitor cell-enriched populations. *Cell* 65:1143-1152.

Morse M A, Lyerly, H K (1998) Immunotherapy of cancer using dendritic cells. *Cytokines Cell Mol Ther* 4:3544.

Morse, M. A., Nair, S., Fernandez-Casal, M., Deng, Y., St Peter, M., Williams, R., Hobeika, A., Mosca, P., Clay, T., Cumming, R. I., Fisher, E., Clavien, P., Proia, A. D., Niedzwiecki, D., Caron, D., and Lyerly, H. K. (2000) *J Clin Oncol* 18(23), 3883-3893.

Myers, R. C., Lau, B. H., Kunihira, D. Y., Torrey, R. R., Woolley, J. L. and Tosk, J. (1989) Modulation of hematoporphyrin derivative-sensitized phototherapy with *Corynebacterium parvum* in murine transitional cell carcinoma. *Urology,* 33:230-235.

Nestle F O, Alijagic S, Gilliet M, Sun Y, Grabbe S, Dummer R, Burg G, Schadendorf D (1998) Vaccination of melanoma patients with peptide- or tumor lysate-pulsed dendritic cells. *Nat Med* 4:328-332.

Nouri-Shirazi, M., Banchereau, J., Bell, D., Burkeholder, S., Kraus, E. T., Davoust, J., and Palucka, K. A. (2000) *J Immunol* 165(7),3797-803.

Nseyo, U. O., Whalen, R. K., Duncan, M. R., Berman, B. and Lundahl, S. (1989) Immune response following photodynamic therapy for bladder cancer. *Proceedings of the Society of Photo-Optical Instrumentation Engineers,* 1065:66-72.

Ochsner, M. (1997) Photophysical and photobiological processes in the photodynamic therapy of tumours. *Journal of Photochemistry and Photobiology. B, Biology,* B-Biology. 39:1-18.

Pardoll, D. M. (1993) New strategies for enhancing the immunogenicity of tumors. *Current Opinion in Immunology,* 5:719-725.

Peron J M, Esche C, Subbotin V M, Maliszewski C, Lotze M T, Shurin M R (1998) FLT3-ligand administration inhibits liver metastases: role of NK cells. *J Immunol* 161:6164-6170.

Poste, G. and Fidler, I. J. (1980) The pathogenesis of cancer metastasis. *Nature,* 283:139-145.

Pulendran, B., Banchereau, J., Burkeholder, S., Kraus, E., Guinet, E., Chalouni, C., Caron, D., Maliszewski, C., Davoust, J., Fay, J., and Palucka, K. (2000) *J Immunol* 165(1), 566-72.

Qin, B., Selman, S. H., Payne, K. M., Keck, R. W. and Metzger, D. W. (1993) Enhanced skin allograft survival after photodynamic therapy. Association with lymphocyte inactivation and macrophage stimulation. *Transplantation,* 56:1481-1486.

Rasko I E J, Metcalf D, Rossner M T, Begley C G, Nicola N A (1995) The receptor flt3/flk-2 ligand: receptor distribution and action on murine haemopoietic cell survival and proliferation. *Leukemia* 9:2058-2066.

Richter, A. M., Kelly, B., Chow, J., Liu, D. J., Towers, G. H. N., Dolphin, D. and Levy, J. G. (1987) Preliminary studies on a more effective phototoxic agent than hematoporphyrin. *Journal of the National Cancer Institute,* 79:1327-1332.

Richter, A. M., Sternberg, E., Waterfield, E., Dolphin, D. and Levy, J. G. (1988) Characterization of benzoporphyrin derivative, a new photosensitizer. *Proceedings of the Society of Photo-Optical Instrumentation Engineers,* 997:132-138.

Richter, A. M., Yip, S., Waterfield, E., Logan, P. M., Slonecker, C. E. and Levy, J. G. (1991) Mouse skin photosensitization with benzoporphyrin derivatives and PHOTOFRIN: macroscopic and microscopic evaluation. *Photochemistry and Photobiology,* 53:281-286.

Robbins, P. F. and Kawakami, Y. (1996) Human tumor antigens recognized by T cell. *Current Opinion in Immunology,* 8:628-636.

Romani, N., Gruner, S., Brang, D., Kampgen, E., Lenz, A., Trockenbacher, B., Konwalinka, G., Fritsch, P. O., Steinman, R. M., and Schuler, G. (1994)*J Exp Med* 180(1), 83-93.

Rosnet O, Marchetto S, deLapeyriere 0, Birnbaum D (1991) Murine Flt3, a gene encoding a novel tyrosine kinase receptor of the PDGFR/CSF1R family. *Oncogene* 6:1641-1650.

Roth, J. A. (1989) Treatment of metastatic cancer Section 2: Treatment of metastatic cancer to lung. In DeVita Jr., V. T., Hellman, S. and Rosenberg, S. A. (eds.), *Cancer: Principles and Practice.* J.B. Lippincott Company, Philadelphia, Vol. 2, pp. 2261-2275.

Sallusto, F., and Lanzavecchia, A. (1994) *J Exp Med* 179(4), 1109-18.

Schuler, G, Steinman R M (1997) Dendritic cells as adjuvants for immune-mediated resistance to tumors. *J Exp Med* 186:1183-1187.

Schultze, J. L., Seamon, M. J., Michalak, S., Gribben, J. G. and Nadler, L. M. (1997) Autologous tumor infiltrating T cells cytotoxic for follicular lymphoma cells can be expanded in vitro. *Blood,* 89:3806-3816.

Section 3: Treatment of metastatic cancer to bone. In DeVita Jr., V. T., Hellman, S. and Rosenberg, S. A. (eds.), *Cancer: Principles and Practice.* J.B. Lippincott Company, Philadelphia, Vol. 2, pp. 2298-2317.

Shaw S G, Maung A A, Steptoe R J, Thomson A W, Vujanovic N L (1998) Expansion of functional natural killer cells in multiple tissue compartments of mice treated with Flt-3-ligand: implications for anti-cancer and anti-viral therapy. *J Immunol* 161:2817-2824.

Shurin M R, Pandharipande P P, Zorina T D, Haluszczak C, Subbotin V M, Hunter O, Brumfield A, Storkus W J, Maraskovsky E, Lotze M T (1997) FLT3 ligand induces the generation of functionally active dendritic cells in mice. *Cell Immunol* 179:174-184.

Soiffer, R., Lynch, T., Mihm, M., Jung, K., Rhuda, C., Schmollinger, J. C., Hodi, F. S., Liebster, L., Lam, P., Mentzer, S., Singer, S., Tanabe, K. K., Cosimi, A. B., Duda, R., Sober, A., Bhan, A., Daley, J., Neuberg, D., Parry, G., Rokovich, J., Richards, L., Drayer, J., Berns, A., Clift, S., Dranoff, G., and et al. (1998) *Proc Natl Acad Sci USA* 95(22), 13141-6

Song W, Kong H L, Carpenter H, Torii H, Granstein S, Raffi S, Moore M A, Crystal R G (1997) Dendritic cells genetically modified with an adenovirus vector encoding the cDNA for a model antigen induce protective and therapeutic antitumor immunity. *J Exp Med* 186, 1247-1256.

Specht J M, Wang G, Do M T, Lam J S, Royal M E, Reeves M E, Rosenberg S A, Hwu P (1997) Dendritic cells retrovirally transduced with a model antigen gene are therapeutically effective against established pulmonary metastases. *J Exp Med* 186:1213-1221.

Steinman R M (1991) The dendritic cell system and its role in immunogenicity. *Ann Rev Immunol* 9:271-296.

Steptoe R J, Fu F, Li W, Drakes M L, Lu L, Demetris A J, Qian S, McKenna H J, Thomson A W (1997) Augmentation of dendritic cells in murine organ donors by Flt3 ligand alters the balance between transplant tolerance and immunity. *J Immunol* 159:5483-5491.

Sugarbaker, P. H. and Kemeny, N. (1989) Treatment of metastatic cancer Section 3: Treatment of metastatic cancer to liver. In DeVita Jr., V. T., Hellman, S. and Rosenberg, S. A. (eds.), *Cancer: Principles and Practice*. J.B. Lippincott Company, Philadelphia, Vol. 2, pp. 2275-2298.

Tao, J., Sanughera, J. S., Pelech, S. L., Wong, G. and Levy, J. G. (1996) Stimulation of stress-activated protein kinase and p38 HOG1 kinase in murine keratinocytes following photodynamic therapy with benzoporphyrin derivative. *Journal of Biological Chemistry*, 271:27107-27115.

Volpert, O. V., Lawler, J. and Bouck, N. P. (1998) A human fibrosarcoma inhibits systemic angiogenesis and the growth of experimental metastases via thrombospondin-1. *Proc Natl Acad Sci USA*, 95:6343-8.

Wang, J., Saffold, S., Cao, X., Krauss, J. and Chen, W. (1998) Eliciting T cell immunity against poorly immunogenic tumors by immunization with dendritic cell-tumor fusion vaccines. *J Immunol*, 161:5516-24.

Weishaupt, K., Gomer, C. J. and Dougherty, T. J. (1976) Identification of singlet oxygen as the cytotoxic agent in photo-inactivation of a murine tumor. *Cancer Research*, 36:2326-2329.

Wright, D. C. and Delaney, T. F. (1989) Treatment of metastatic cancer Section 1: Treatment of metastatic cancer to the brain. In DeVita Jr., V. T., Hellman, S. and Rosenberg, S. A. (eds.), *Cancer: Principles and Practice*. J.B. Lippincott Company, Philadelphia, Vol. 2, pp. 2245-2261.

Yamamoto, N., Hoober, J. K. and Yamamoto, S. (1992) Tumoricidal capacities of macrophages photodynamically activated with hematoporphyrin derivative. *Photochemistry and Photobiology*, 56:245-250.

Yamamoto, N., Sery, T. W., Hoober, J. K., Willett, N. P. and Lindsay, D. D. (1994) Effectiveness of photofrin II in activation of macrophages and in vitro killing of retinoblastoma cells. *Photochemistry and Photobiology*, 60:160-164.

Young J W, Inaba K (1996) Dendritic cells as adjuvants for Class I major histocompatibility complex-restricted anti-tumour immunity. *J Exp Med* 183:7-11.

Zitvogel L, Mayordomo J I, Tjandrawan T, DeLeo A B, Clarke M R, Lotze M T, Stokus W J (1996) Therapy of murine tumors with tumor peptide-pulsed dendritic cells: dependence on T cells, B7 costimulation, and T helper cell 1-associated cytokines. *J Exp Med* 183:87-97.

Appendix A: Adjuvant Classification

PARTICULATE ADJUVANTS
    exist as microscopic, insoluble particles
    generally, the immunogen must be incorporated into or
    associated with the particle.
  A. Mineral-based
    insoluble, gel-like precipitate
    mineral formulations are the only adjuvants that are
    considered safe and effective for use in
    human vaccines
    i. Aluminum hydroxide (Alhydrogel)
      Superfos chemicals
        a. SBAS4
          Aluminum salt combined with
          monophosphoryl lipid A (MPL)
          SmithKline Beecham
    ii. Aluminum phosphate (Adju-Phos)
      Superfos chemicals
    ii. Calcium phosphate
      Superfos chemicals
  B. Water-in-oil emulsions
    microdroplets of water, stabilized by surfactant in a continuous
    oil phase
    i. Freund's Complete Adjuvant (FCA)
      a mixture of a non-metabolizable oil (mineral oil),
      a surfactant (Arlacel A), and mycobacteria
      (*M. tuberculosis* or *M. butyricum* in Modified FCA)
      Superfos chemicals
    ii. Freund's Incomplete Adjuvant (FIA)
      has the same oil/surfactant mixture as FCA but
      does not contain any mycobacteria
    iii. Montanide Incomplete Seppic Adjuvant (ISA) Adjuvants
      a group of oil/surfactant based adjuvants in which
      different surfactants are combined with either a
      non-metabolizable mineral oil, a metabolizable
      oil, or a mixture of the two. They are prepared
      for use as an emulsion with aqueous Ag solution.
      The surfactant for Montanide ISA 50 is mannide
      oleate, a major component of the surfactant in
      Freund's adjuvants. The surfactants of the Montanide
      group undergo strict quality control to guard
      against contamination by any substances that could
      cause excessive inflammation, as has been found
      for some lots of Arlacel A used in Freund's adjuvant.
      The various Montanide ISA group of adjuvants are
      used as water-in-oil emulsions, oil-in-water
      emulsions, or water-in-oil-in-water emulsions.
      The different adjuvants accommodate different
      aqueous phase/oil phase ratios, because of the
      variety of surfactant and oil combinations. The
      performance of these adjuvants is said to be
      similar to Incomplete Freunds Adjuvant for
      antibody production; however the inflammatory
      response is usually less. Seppic, Paris, France
  C. Oil-in-water emulsions
    microdroplets of squalene or squalane, stabilized with surfactants
    in a continuous water phase, developed for human clinical trials
    when combined with immunomodulators
    i. Ribi Adjuvant System (RAS)
      4 components: (1) monophosphoryl lipid A (MPL);
      (2) trehalose dimycolate (TDM); (3) cell wall
      skeletons (CWS); (4) *S. typhimurium* mitogen (STM)
      Ribi ImmunoChem Research, Inc.
    ii. MF59
      originally developed with N-acetyl-muramyl-L-
      alanyl-2-(1',2'-dipalmitolyl-sn-glycero-3'-
      phospho)ethylamide (MTP-PE) however when antibody titer was endpoint, MTP-PE was not required
      for adjuvant activity Chiron Corp.
    iii. SBAS4
      combination of monophosphoryl lipid A (MPL),
      QS21, and a proprietary oil in water emulsion
      SmithKIine Beecham

| Appendix A: Adjuvant Classification |
|---|
| iv. DETOX ™<br>    active ingredients include MPL ®-(derivative of<br>    the lipid A molecule found in gram negative<br>    bacteria) and mycobacterial cell wall skeleton<br>    Corixa Corporation<br>v. DETOX ™ B-SE (Enhanzyn ™) for investigational use<br>    is supplied in clear glass vials.<br>    Each vial contains: 145 micrograms CWS from<br>    *M. phlei*, 25 micrograms MPL from S. minnesota<br>    R595, 8.1 milligrams Squalane F, 0.38 milligrams<br>    Polysorbate 80 (USP/NF), 1.62 milligrams Soy<br>    Lecithin (NF), and 88 micrograms Sterile Water<br>    for Injection (USP)<br>    DETOX ™ B-SE must be stored refrigerated<br>    between 2 and 8° C.<br>D. Immune stimulating complexes (ISCOM)<br>    open, cage-like structure resulting from the interaction of Quil-A<br>    with cholesterol and phosphatidycholine, human clinical trials<br>E. Liposomes<br>    single or multilamellar bilayer membrane vesicles comprised of<br>    cholesterol and phospholipid<br>    the immunogen may be membrane-bound or within the<br>    intermembrane spaces<br>F. Nano- and microparticles<br>    solid particles, biocompatible and biodegradable, synthetic<br>    polymers of cyanoacrylates, polycatide coglycolide (PLG)<br>    copolymer, antigen must be formulated with particle<br>NON-PARTICULATE ADJUVANTS<br>A. Muramyl dipeptide (MDP) and derivatives: Adjuvant peptides<br>    N-acetyl muramyl-L-alanyl-D-isoglutamine is the active<br>    component of peptidoglycan extracted from *Mycobacterium*,<br>    derivatives are less toxic<br>    i. threonyl MDP<br>    ii. murabutide,N-acetylglucosaminyl-MDP (GMDP)<br>      a. Gerbu Adjuvant<br>        Alternative to FCA. Oil is replaced by<br>        water-soluble, aliphatic quaternary amines<br>        or bio-degradable esterquats. *Mycobacterium*<br>        is replaced by GMDP.<br>        Gerbu Biotechnik GmbH, Gaiberg, Germany<br>        C-C Biotech<br>        16766 Espola Road<br>        Poway, CA 92064<br>        USA<br>    iii. murametide<br>    iv. nor-MDP<br>B. Non-ionic block copolymers<br>    polymers composed of a region of hydrophobic polyoxypropylene<br>    (POP) flanked by regions of hydrophilic polyoxyethylene<br>    (POE), not biodegradable<br>    i. TiterMax ™<br>      CytRx Corporation<br>    iv. Syntex Adjuvant Formulation-1 (SAF-1)<br>      Roche Bioscience (formerly Syntex Corp., Palo Alto, CA)<br>    iv. SAF-2<br>C. Saponins<br>    extract of *Quillaia saponaria* tree, saponin is crude extract of<br>    triterpenoids<br>    i. Quil A<br>      Partially purified saponin<br>    ii. Spikoside<br>      Partially purified saponin<br>    iii. QS21 (Stimulon)<br>      Purified, defined entity<br>      Aquila Biopharmaceuticals, Inc. (formerly<br>      Cambridge Biotech Corporation)<br>    iv. ISCOPREP ™ 703<br>      Purified, defined entity<br>D. Lipid A and derivatives<br>    disaccharide of glucosamine with two phosphate groups and five<br>    or six fatty acid chains ($C_{12}$ to $C_{16}$ in length)<br>    i. monophosphoryl lipid A (MPL)<br>      removal of the 1' phosphate group from lipid A<br>      gives MPL |

| Appendix A: Adjuvant Classification |
|---|
| E. Cytokines<br>F. Carbohydrate polymers<br>    polymers of mannose and β1-3 glucose<br>    proposed as human vaccine adjuvants either mixed with or<br>    conjugated with immunogen<br>    stimulate macrophages and dendritic cells<br>G. Derivatized polysaccharides<br>    high molecular weight sulphated dextrans proposed as human<br>    vaccine adjuvants<br>H. Bacterial toxins<br>    potent mucosal adjuvants in animal models |

We claim:

1. A method of treating metastasized tumor lesions in a human subject, said method comprising:
   identifying a human subject having metastasized tumor lesion(s) of a discrete tumor,
   administering to said human subject effective amounts of a green porphyrin photosensitizer and an immuno-adjuvant, wherein said effective amounts destroy metastasized tumor cells via immuno-adjuvant photodynamic therapy without photoactivation treatment of said metastasized tumor cells, and
   irradiating the subject at the site of the discrete tumor with light absorbed by the photosensitizer,
   whereby metastasized tumor lesion(s) in the subject is/are treated by said immuno-adjuvant photodynamic therapy.

2. The method of claim 1, wherein the subject has previously undergone cancer or tumor therapy.

3. The method of claim 1, wherein the effective amount of the photosensitizer is in the range of 0.05 to 10 mg/kg.

4. The method of claim 3, wherein the effective amount of the photosensitizer is in the range of 0.05 to 1 mg/kg.

5. The method of claim 3, wherein the effective amount of the photosensitizer is in the range of 1 to 10 mg/kg.

6. The method of claim 1, wherein the photosensitizer is administered intravenously and the immuno-adjuvant is administered after irradiation.

7. The method of claim 1, wherein the photosensitizer is administered intravenously or intratumorally.

8. The method of claim 1, wherein the photosensitizer is administered, and the subject irradiated, before administration of the immuno-adjuvant.

9. The method of claim 1, wherein the immuno-adjuvant is administered systemically.

10. The method of claim 1, further comprising an additional irradiation, before irradiation with light absorbed by the photosensitizer, with light of a wavelength which improves penetration of the absorbed light.

11. The method of claim 1, wherein the immuno-adjuvant comprises mycobacterial cell wall skeleton and/or lipid A from a gram negative bacterium.

12. The method of claim 11, wherein said lipid A is de-3-O-acylated lipid A.

13. The method of claim 6, further comprising systemic administration of an additional amount of immuno-adjuvant to the subject.

14. The method of claim 1, wherein the green porphyrin photosensitizer is a benzoporphyrin derivative (BPD).

15. The method of claim 14, wherein the BPD is BPD-MA, EA6, or B3.

16. The method of claim 14, wherein the BPD is BPD-MA.

17. The method of claim 1, wherein the metastasized tumor lesion(s) have been identified in a lymph node of the subject.

18. The method of claim 1, wherein the metastasized tumor lesion(s) have been identified in the liver of the subject.

* * * * *